United States Patent
Sova et al.

(10) Patent No.: US 9,174,930 B2
(45) Date of Patent: Nov. 3, 2015

(54) PREPARATION OF SITAGLIPTIN INTERMEDIATES

(75) Inventors: Matej Sova, Ljubljana (SI); Zdenko Casar, Ljubljana (SI); Gaj Stavber, Ljubljana (SI)

(73) Assignee: LEK PHARMACEUTICALS D.D., Ljubljana (SI)

( * ) Notice: Subject to any disclaimer, the term of this patent is extended or adjusted under 35 U.S.C. 154(b) by 0 days.

(21) Appl. No.: 14/110,688

(22) PCT Filed: Apr. 6, 2012

(86) PCT No.: PCT/EP2012/001562
§ 371 (c)(1),
(2), (4) Date: Mar. 14, 2014

(87) PCT Pub. No.: WO2012/136383
PCT Pub. Date: Oct. 11, 2012

(65) Prior Publication Data
US 2014/0213810 A1  Jul. 31, 2014

(30) Foreign Application Priority Data

Apr. 8, 2011 (EP) .................................... 11161611

(51) Int. Cl.
| C07C 69/76 | (2006.01) |
| C07C 229/30 | (2006.01) |
| C07F 5/04 | (2006.01) |
| C07C 67/31 | (2006.01) |
| C07C 67/343 | (2006.01) |
| C07C 227/06 | (2006.01) |
| C07C 227/08 | (2006.01) |
| C07C 231/06 | (2006.01) |
| C07C 233/47 | (2006.01) |
| C07F 5/02 | (2006.01) |
| C07B 53/00 | (2006.01) |

(52) U.S. Cl.
CPC .............. *C07C 229/30* (2013.01); *C07B 53/00* (2013.01); *C07C 67/31* (2013.01); *C07C 67/343* (2013.01); *C07C 227/06* (2013.01); *C07C 227/08* (2013.01); *C07C 231/06* (2013.01); *C07C 233/47* (2013.01); *C07F 5/02* (2013.01); *C07F 5/025* (2013.01); *C07F 5/027* (2013.01); *C07F 5/04* (2013.01)

(58) Field of Classification Search
CPC .......... C07C 69/76; C07C 229/30; C07F 5/04
See application file for complete search history.

(56) References Cited

U.S. PATENT DOCUMENTS

| 2006/0052382 A1 | 3/2006 | Duffy et al. |
| 2009/0192326 A1 | 7/2009 | Perlman et al. |

FOREIGN PATENT DOCUMENTS

| WO | WO 03/004498 A1 | 1/2003 |
| WO | WO 2004/085378 A1 | 10/2004 |
| WO | WO 2004/085661 A2 | 10/2004 |
| WO | WO 2004/087650 A2 | 10/2004 |
| WO | WO 2004/087650 A3 | 10/2004 |
| WO | WO 2005/097733 A1 | 10/2005 |
| WO | WO 2006/081151 A1 | 8/2006 |
| WO | WO 2009/045507 A2 | 4/2009 |
| WO | WO 2009/045507 A3 | 4/2009 |
| WO | WO 2009/064476 A1 | 5/2009 |
| WO | WO 2010/078440 A1 | 7/2010 |
| WO | WO 2010/122578 A2 | 10/2010 |

OTHER PUBLICATIONS

Database Registry Chemical Abstracts Service, Columbus, Ohio, Accession No. RN 1234321-83-5, Entered STN: Jul. 29, 2010.*
Feng et al., "The asymmetric synthesis of Sitagliptin, a selective dipeptidyl peptides IV inhibitor for the treatment of type 2 diabetes," Journal of Chemical Research, Science Reviews Ltd., GB, vol. 34, Apr. 1, 2010, pp. 230-232.
International Search Report & Written Opinion issued in PCT/EP2012/001562, dated Jan. 28, 2013, 15 pages.
Martin et al., "Cross-Coupling of Alkyl Halides with Aryl Grignard Reagents Catalyzed by a Low-Valent Iron Complex," Angew. Chemie. Int. Ed., vol. 43, 2004, pp. 3955-3957.
Desai, "Sitagliptin Manufacture: A Compelling Tale of Green Chemistry, Process Intensification, and Industrial Asymmetric Catalysis", Angew. Chem. Int. Ed., vol. 50, pp. 1974-1976 (2011).
Hansen, K.B., et al., "First Generation Process for the Preparation of the DPP-IV Inhibitor Sitagliptin", Organic Process Research & Development, vol. 9, No. 5, pp. 634-639 (2005).
Hansen, K.B., et al., "Highly Efficient Asymmetric Synthesis of Sitagliptin", J. Am. Chem. Soc., vol. 131, pp. 8798-8804 (2009).
Hsiao, Y., et al., "Highly Efficient Synthesis of Beta-Amino Acid Derivatives via Asymmetric Hydrogenation of Unprotected Enamines", J. Am. Chem. Soc., vol. 126, pp. 9918-9919 (2004).
Kubryl, M. et al., "Application of the asymmetric hydrogenation of enamines to the preparation of a beta-amino acid pharmacophore", Tetrahedron: Asymmetry, vol. 17, pp. 205-209 (2006).
Savile, C. K., et al., "Biocatalytic Asymmetric Synthesis of Chiral Amines from Ketones Applied to Sitagliptin Manufacture", Science, vol. 329, pp. 305-309 (2010).

* cited by examiner

*Primary Examiner* — Samantha Shterengarts
(74) *Attorney, Agent, or Firm* — Arent Fox LLP

(57) ABSTRACT

The invention relates to the preparation of chiral compounds, in particular to the preparation of chiral compounds which may be used as intermediates for the preparation of antidiabetic agents, preferably sitagliptin.

20 Claims, No Drawings

PREPARATION OF SITAGLIPTIN INTERMEDIATES

CROSS-REFERENCE TO RELATED APPLICATION

This application is a National Stage entry of International Application No. PCT/EP2012/001562, filed Apr. 6, 2012, which claims priority to European Application No.11161611.6, filed Apr. 8, 2011, the entire specifications, claims and drawings of which are incorporated herewith by reference.

FIELD OF THE INVENTION

The present invention relates to the preparation of chiral compounds, in particular to the preparation of chiral compounds which may be used as intermediates for the preparation of anti-diabetic agents, preferably sitagliptin.

BACKGROUND PRIOR ART

Type II diabetes mellitus (T2DM) is a global epidemic. Therefore, the research is oriented in the development of selective inhibitors of the enzyme DPP-IV as a promising new treatment for the type II diabetes.

Sitagliptin (CAS Registry Number 486460-32-6. IUPAC Name: (R)-4-oxo-4-[3-(trifluoromethyl)-5,6-dihydro[1,2,4]triazolo[4,3-a]pyrazin-7(8H)-yl]-1-(2,4,5-trifluorophenyl)butan-2-amin) is an anti-diabetic agent and a potent inhibitor of the DPP-IV. It is represented by the structure:

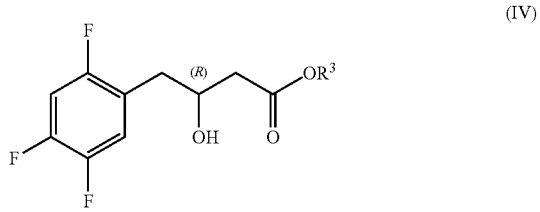

There is a constant search for improved synthetic protocols for key intermediates, in particular β-amino acid intermediates of the formula I,

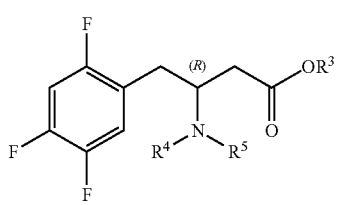

and β-hydroxy intermediates of the formula IV

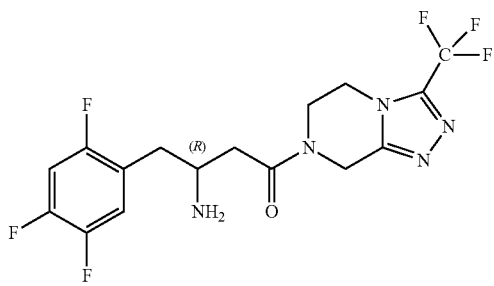

for the synthesis of sitagliptin.

WO 03/004498 disclose a method for producing the carboxylic acid of the β-amino acid intermediate of the formula I, which is performed through a 2,3,5-trifluorobenzylbromide intermediate, where enantioselectivity was induced by the use of unusual dihydropyrazine chiral auxiliaries. In the last steps, diazomethane, which is an explosive reagent, and stoichoimetric amounts of silver salts are included in the synthetic protocol which are very expensive and therefore unsuitable reagents for industrial synthesis.

Other synthetic approaches include asymmetric hydrogenation of β-enamino acid intermediates. The asymmetric hydrogenation reactions are conducted in the presence of expensive metal catalysts like rhodium in combination with chiral phosphine/diphosphine ligands (WO 03/004498, Kubryl, M.; et. al. *Tetrahedron Asymmetry* 2006, 17, 205). In some cases also expensive ruthenium metal catalysts are used (WO 09/064476, WO 04/085378, WO 05/097733, WO 06/081151, Hsiao, Y.; et. al. *J. Am. Chem. Soc.*, 2004, 126, 9918). Hydrogenation with cheaper achiral catalysts involving a chiral derivatization of enamines is also known (WO 04/085661).

Also known are synthetic strategies, which are based on the chemocatalytic selective reduction of β-keto esters in the presence of ruthenium or rhodium diphosphine chiral catalysts (WO 04/087650, US 2009/0192326; US 2006/0052382; Hansen, K. B.; et. al. *J. Am. Chem. Soc.* 2009, 131, 8798.; Hansen K. B.; et. al. *Org. Process Res. Dev.* 2005, 9, 634-639).

WO 09/045507 discloses a biocatalytic approach to sitagliptin where an enantioselective step was performed using an appropriate enzymes (ketoreductase) for the asymmetric reduction of the β-carbonyl part of the molecule to form than the β-hydroxy intermediates of the formula IV. The transformation of the obtained chiral hydroxyl intermediates to the final sitagliptin precursors was performed via azetidinone intermediates. It is well known that this step is very difficult to establish. Disadvantages of these protocols are also: reactions at high pressures (250 psi), the use of very expensive metal chiral catalysts (Rh or Ru), low stereoselectivity and product contamination with rhodium and consequently hard purification protocols of final compound.

WO 09/045507 discloses difficult protocols for the synthesis of the β-hydroxy intermediate of the formula IV and the β-amino acid intermediate of the formula I.

It has been also shown that rhodium or ruthenium asymmetric catalytic hydrogenation of β-keto esters through enamines can be replaced by an efficient biocatalytic process using special enzymes transaminases, which improve the efficiency of sitagliptin manufacturing up to 99.95% enantiomeric excess (Savile, C. K.; et. al. *Science* 2010, 329, 305 and references cited therein). This enzymatic route features direct amination of the prositagliptin ketone to provide the enantiopure sitagliptin, followed by phosphate salt formation to provide the final sitagliptin phosphate. It is well known that enzymatic reactions offer an environmentally friendly approach to the synthesis of final molecules but on the other hand the availability and especially price of special enzymes (isolation protocols etc.) represent an inconsiderable disadvantage of a biocatalytic process.

There is also disclosed an intermediate of the formula II

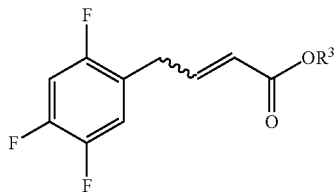

(II)

with $R^3$ being methyl, but no experimental procedure, no evidence and any other signs are devoted to this intermediate. All synthetic strategies disclosed in WO 2010/122578 are experimentally complicated, involve relatively many synthetic steps and some of them are conducted under extreme reaction conditions (temperature up to −50° C.; dry conditions etc.). The efficiency and especially the selectivity of some individual synthetic steps are modest and consequently influence the lower overall yields of the process.

Liu et al. discloses an asymmetric synthesis of sitagliptin over 9-10 steps, with the overall 31% yield and 99.5% enantiomeric excess (Liu, F.; et. al. *J. Chem. Res.* 2010, 34, 230-232.) The synthetic strategy involving also an intermediate of formula II, presents synthetic approach to sitagliptin but on the other hand offers also a lot of disadvantages. One of these disadvantages is the long and complicated process to obtain the intermediate of the formula II.

Therefore, it was an object of the present invention to provide an improved process for the preparation of an intermediate of formula I.

It was another object of the present invention to provide an improved process for the preparation of an intermediate of formula I starting from of the intermediate of the formula II.

It was a further object of the present invention to provide an improved process for the preparation of an intermediate of formula IV.

It was another object of the present invention to provide an improved process for the preparation of an intermediate of formula IV starting from the intermediate of the formula II.

It was yet another object of the present invention to provide an improved and simple process for the preparation of an intermediate of the formula II. In particular, the object was to provide an improved and simple one-pot process for the preparation of an intermediate of the formula II using environment friendly reagents.

It was yet another object of the present invention to provide new intermediates for the preparation of anti-diabetic agents, preferably sitagliptin.

SUMMARY OF THE INVENTION

According to one aspect the present invention relates to a process for the preparation of an intermediate of formula I

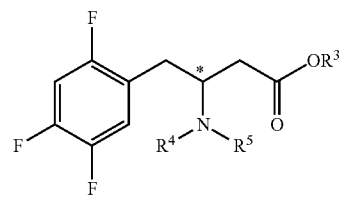

(I)

wherein the stereogenic center marked with an * is either in (R)- or (S)-configuration at marked center, or it is in racemic form, and
wherein $R^4$ and $R^5$ are identical or different, and are independently selected from
(i) hydrogen;
(ii) alkyl residues optionally chiral, having from 1 to 12 carbon atoms, wherein the alkyl residues are optionally aryl and/or aryloxy substituted;
(iii) alkyloxy residues optionally chiral, having from 1 to 12 carbon atoms, wherein the alkyloxy residues are optionally aryl substituted;
(iv) aryl residues optionally chiral, having from 6 to 24 carbon atoms, wherein the aryl residues are optionally alkyl and/or alkyloxy substituted;
(v) aryloxy residues optionally chiral, having from 6 to 24 carbon atoms, wherein the aryloxy residues are optionally alkyl substituted;
(vi) benzyl;
(vii) alkaloyl residues optionally chiral, having from 2 to 13 carbon atoms, wherein the alkaloyl residues are optionally aryl substituted;
(viii) aroyl residues optionally chiral, having from 7 to 25 carbon atoms, wherein the aryloxy residues are optionally alkyl substituted;
(ix) alkoxycarbonyl residues optionally chiral, having from 2 to 13 carbon atoms;
(x) aryloxycarbonyl residues optionally chiral, having from 7 to 25 carbon atoms; and
(xi) tosyl;
wherein $R^3$ is selected from alkyl residues having from 1 to 6 carbon atoms;
the process comprising the steps of:
(a) providing an intermediate of formula II

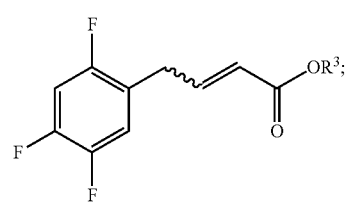

(II)

(b) reacting the intermediate of formula II with a borating agent in a suitable solvent to obtain an intermediate of formula III,

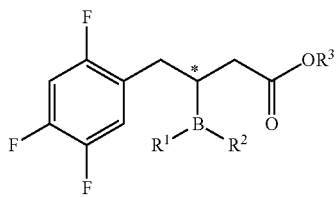

(III)

wherein the stereogenic center marked with an * is either in (R)- or (S)-configuration at marked center, or it is in racemic form, and
wherein $R^1$ and $R^2$ are identical or different, and are selected from
(i) alkyl or alkoxy residues, each having from 1 to 12 carbon atoms, wherein each alkyl or alkoxy residue is optionally aryl substituted,
(ii) aryl or aryloxy residues, each having from 6 to 14 carbon atoms, wherein each aryl or aryloxy residue is optionally alkyl substituted;
(iii) halides; and
(iv) wherein $R^1$ and $R^2$ optionally form a chiral or non-chiral 5 to 10, particularly 5 to 6, membered mono or bicyclic ring, wherein the ring is optionally substituted at least one position with an alkyl residue having from 1 to 12 carbon atoms and/or an aryl residue having from 6 to 14 carbon atoms, and wherein $R^1$ and $R^2$ optionally form an O-benzenedioxy residue; and wherein $R^3$ is selected from alkyl residues having from 1 to 6 carbon atoms;
(c) converting the intermediate of formula III to the intermediate of formula I.

According to another aspect of the present invention there is provided an intermediate of formula III, and the isomers, and the isomer mixtures thereof,

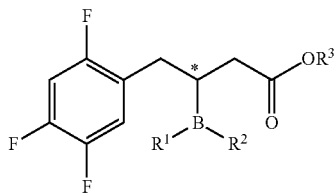

(III)

wherein $R^1$ and $R^2$ are identical or different, and are selected from
(i) alkyl or alkoxy residues, each having from 1 to 12 carbon atoms, wherein each alkyl or alkoxy residue is optionally aryl substituted;
(ii) aryl or aryloxy residues, each having from 6 to 14 carbon atoms, wherein each aryl or aryloxy residue is optionally alkyl substituted;
(iii) halides; and
(iv) wherein $R^1$ and $R^2$ optionally form a chiral or non-chiral 5 to 10, particularly 5 to 6, membered mono or bicyclic ring, wherein the ring is optionally substituted at least one position with an alkyl residue having from 1 to 12 carbon atoms and/or an aryl residue having from 6 to 14 carbon atoms, wherein $R^1$ and $R^2$ optionally from a O-benzenedioxy residue, and wherein $R^3$ is selected from alkyl residues having from 1 to 6 carbon atoms.

In still another aspect, there is provided a new simple process for the preparation of an intermediate of formula II

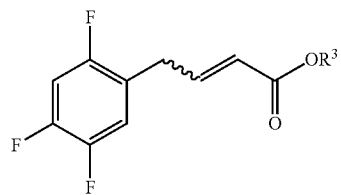

(II)

wherein $R^3$ is selected from alkyl residues having from 1 to 6 carbon atoms;
the process comprises or consists the steps of:
(a) providing an intermediate of formula V

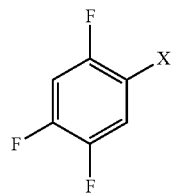

(V)

(b) reacting the intermediate of formula V, wherein X is selected from Cl, Br, I, and is preferably Br with a Grignard compound, or with magnesium in the presence of an activating agent, wherein the activating agent is particularly selected from iodine, methyl iodide, 1,2-dibromoethane, and any combination thereof;
in a suitable solvent to obtain an intermediate of formula VI

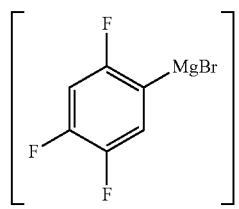

(VI)

(c) reacting the intermediate of formula VI with a compound of formula VII

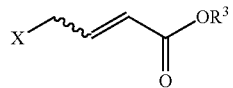

(VII)

wherein X is selected from Cl, Br, and I, and is preferably Br,
in a metal catalyzed cross-coupling process in a suitable solvent to obtain the intermediate of formula II.

The present invention represents an improvement over the known methodologies, since the reactions are conducted under mild reaction conditions, especially the step to form intermediate of formula (III), simple and the commercially available reagents may be used and less reaction steps considering previous patents and literature are necessary.

The present invention represents an improvement over the known methodologies to obtain an intermediate of formula II as only two steps performed as one-pot process are needed. Therewith a short and simple process for the preparation of an intermediate of formula (II) is provided.

Other aspects and further preferred embodiments are set out as defined in the items and in the detailed description of the invention.

DEFINITIONS

The term "intermediate" as used herein shall be understood as including compounds which are isolated from a reaction mixture and compounds which are not isolated from a reaction mixture.

The term "room temperature" used herein will be understood be the person skilled in the art as referring to a temperature between about 20° C. and about 25° C., particularly between 20° C. and 25° C.

DETAILED DESCRIPTION OF THE INVENTION

Process for the Preparation of an Intermediate of Formula I

According to one aspect the present invention relates to a process for the preparation of an intermediate of formula I

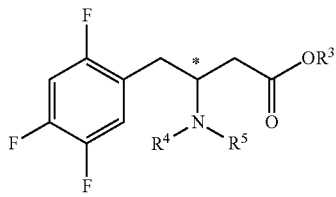

(I)

wherein the stereogenic center marked with an * is either in (R)- or (S)-configuration at marked center, or it is in racemic form, and wherein $R^4$ and $R^5$ are identical or different, and are independently selected from
(i) hydrogen;
(ii) alkyl residues optionally chiral, having from 1 to 12 carbon atoms, wherein the alkyl residues are optionally aryl and/or aryloxy substituted;
(iii) alkyloxy residues optionally chiral, having from 1 to 12 carbon atoms, wherein the alkyloxy residues are optionally aryl substituted;
(iv) aryl residues optionally chiral, having from 6 to 24 carbon atoms, wherein the aryl residues are optionally alkyl and/or alkyloxy substituted;
(v) aryloxy residues optionally chiral, having from 6 to 24 carbon atoms, wherein the aryloxy residues are optionally alkyl substituted;
(vi) benzyl;
(vii) alkaloyl residues optionally chiral, having from 2 to 13 carbon atoms, wherein the alkaloyl residues are optionally aryl substituted;
(viii) aroyl residues optionally chiral, having from 7 to 25 carbon atoms, wherein the aryloxy residues are optionally alkyl substituted; and
(ix) alkoxycarbonyl residues optionally chiral, having from 2 to 13 carbon atoms;

(x) aryloxycarbonyl residues optionally chiral, having from 7 to 25 carbon atoms; and
(xi) tosyl;
wherein $R^3$ is selected from alkyl residues having from 1 to 6 carbon atoms;
the process comprising the steps of:
(a) providing an intermediate of formula II

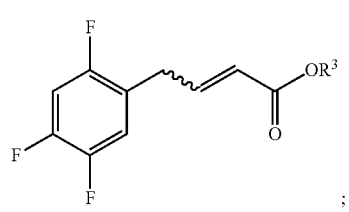

(II)

;

(b) reacting the intermediate of formula II with a borating agent in a suitable solvent to obtain an intermediate of formula III,

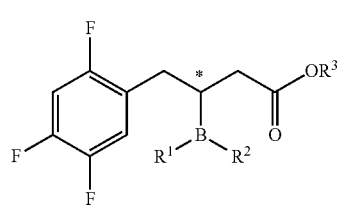

(III)

wherein the stereogenic center marked with an * is either in (R)- or (S)-configuration at marked center, or it is in racemic form, and wherein $R^1$ and $R^2$ are identical or different, and are selected from
(i) alkyl or alkoxy residues, each having from 1 to 12 carbon atoms, wherein each alkyl or alkoxy residue is optionally aryl substituted,
(ii) aryl or aryloxy residues, each having from 6 to 14 carbon atoms, wherein each aryl or aryloxy residue is optionally alkyl substituted;
(iii) halides; and
(iv) wherein $R^1$ and $R^2$ optionally form a chiral or non-chiral 5 to 10, particularly 5 to 6, membered mono or bicyclic ring, wherein the ring is optionally substituted at least one position with an alkyl residue having from 1 to 12 carbon atoms and/or an aryl residue having from 6 to 14 carbon atoms, and wherein $R^1$ and $R^2$ optionally form an O-benzenedioxy residue and wherein $R^3$ is same as above;
(c) converting the intermediate of formula III to the intermediate of formula I.

In a preferred embodiment, $R^4$ and $R^5$ are identical, and are selected from
(i) hydrogen;
(ii) alkyl residues optionally chiral, having from 1 to 12 carbon atoms, wherein the alkyl residues are optionally aryl and/or aryloxy substituted;
(iii) alkyloxy residues optionally chiral, having from 1 to 12 carbon atoms, wherein the alkyloxy residues are optionally aryl substituted;
(iv) aryl residues optionally chiral, having from 6 to 24 carbon atoms, wherein the aryl residues are optionally alkyl and/or alkyloxy substituted;

(v) aryloxy residues optionally chiral, having from 6 to 24 carbon atoms, wherein the aryloxy residues are optionally alkyl substituted;
(vi) benzyl;
(vii) alkaloyl residues optionally chiral, having from 2 to 13 carbon atoms, wherein the alkaloyl residues are optionally aryl substituted;
(viii) aroyl residues optionally chiral, having from 7 to 25 carbon atoms, wherein the aryloxy residues are optionally alkyl substituted; and
(ix) alkoxycarbonyl residues optionally chiral, having from 2 to 13 carbon atoms;
(x) aryloxycarbonyl residues optionally chiral, having from 7 to 25 carbon atoms; and
(xi) tosyl.

In a particularly preferred embodiment, $R^4$ and $R^5$ are hydrogen. In another particularly preferred embodiment, $R^4$ and $R^5$ are N-α-methylbenzyl.

In another preferred embodiment, $R^4$ and $R^5$ are different, and are independently selected from
(i) hydrogen;
(ii) alkyl residues optionally chiral, having from 1 to 12 carbon atoms, wherein the alkyl residues are optionally aryl substituted;
(iii) alkyloxy residues optionally chiral, having from 1 to 12 carbon atoms, wherein the alkyloxy residues are optionally aryl and/or aryloxy substituted;
(iv) aryl residues optionally chiral, having from 6 to 24 carbon atoms, wherein the aryl residues are optionally alkyl and/or alkyloxy substituted;
(v) aryloxy residues optionally chiral, having from 6 to 24 carbon atoms, wherein the aryloxy residues are optionally alkyl substituted;
(vi) benzyl;
(vii) alkaloyl residues optionally chiral, having from 2 to 13 carbon atoms, wherein the alkaloyl residues are optionally aryl substituted;
(viii) aroyl residues optionally chiral, having from 7 to 25 carbon atoms, wherein the aryloxy residues are optionally alkyl substituted; and
(ix) alkoxycarbonyl optionally chiral residues, having from 2 to 13 carbon atoms;
(x) aryloxycarbonyl residues optionally chiral, having from 7 to 25 carbon atoms; and
(xi) tosyl.

In a particularly preferred embodiment, $R^4$ is hydrogen and $R^5$ is tosyl. In another particularly preferred embodiment, $R^4$ is hydrogen and $R^5$ is benzyl. In a further particularly preferred embodiment, $R^4$ is hydrogen and $R^5$ is O-benzyl. In a further particularly preferred embodiment, $R^4$ is hydrogen and $R^5$ is O-methyl. In still a further particularly preferred embodiment, $R^4$ is benzyl and $R^5$ is N-α-methylbenzyl. In a further particularly preferred embodiment, $R^4$ is hydrogen and $R^5$ is tert-butyl-oxy-carbonyl. In still a further particularly preferred embodiment, $R^4$ is hydrogen and $R^5$ is benzyl-oxy-carbonyl. In still a further particularly preferred embodiment, $R^4$ is hydrogen and $R^5$ is benzoyl. In still a further particularly preferred embodiment, $R^4$ is hydrogen and $R^5$ is acetyl. In still a further particularly preferred embodiment, $R^4$ is hydrogen and $R^5$ is N-α-methylbenzyl. In a further particularly preferred embodiment, $R^4$ is hydrogen and $R^5$ is phenyl-O-methyl.

The chiral aryl residues defined for $R^4$ and $R^5$ are typically selected from N-α-methylbenzyl, N-bis[α-methylbenzyl], 2-methoxybenzyl-1-phenylethyl, 3,4-dimethoxybenzyl-1-phenylethyl, and 1-benzyl-1-phenylethyl.

In the intermediate of formula I, the intermediate of formula II, and in the intermediate of formula III, $R^3$ is typically selected from methyl, ethyl, propyl, cyclopropyl, butyl, pentyl, hexyl, isopropyl, isopentyl, tert-butyl, and is particularly methyl. In a particularly preferred embodiment $R^3$ of the intermediate of formula II is methyl (intermediate of formula IIa).

In particularly preferred embodiments, the intermediate of formula I is

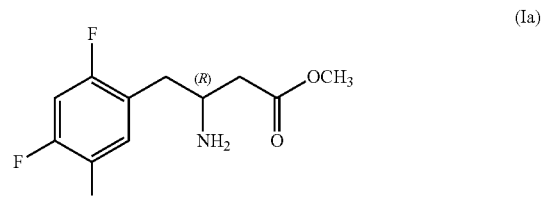

(Ia)

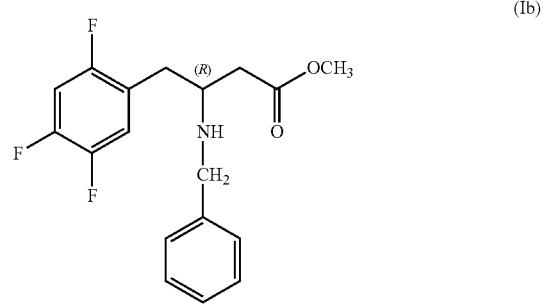

(Ib)

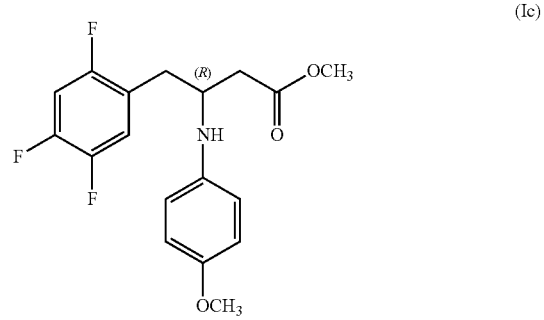

(Ic)

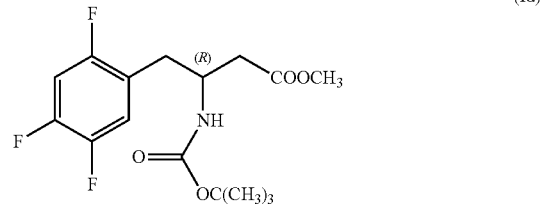

(Id)

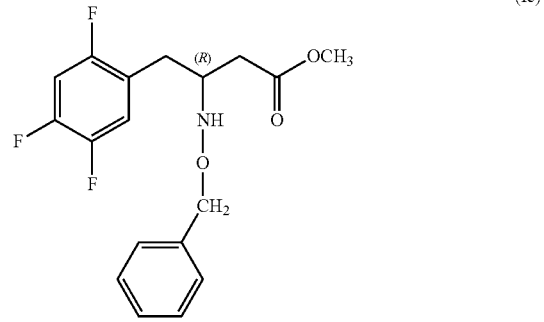

(Ie)

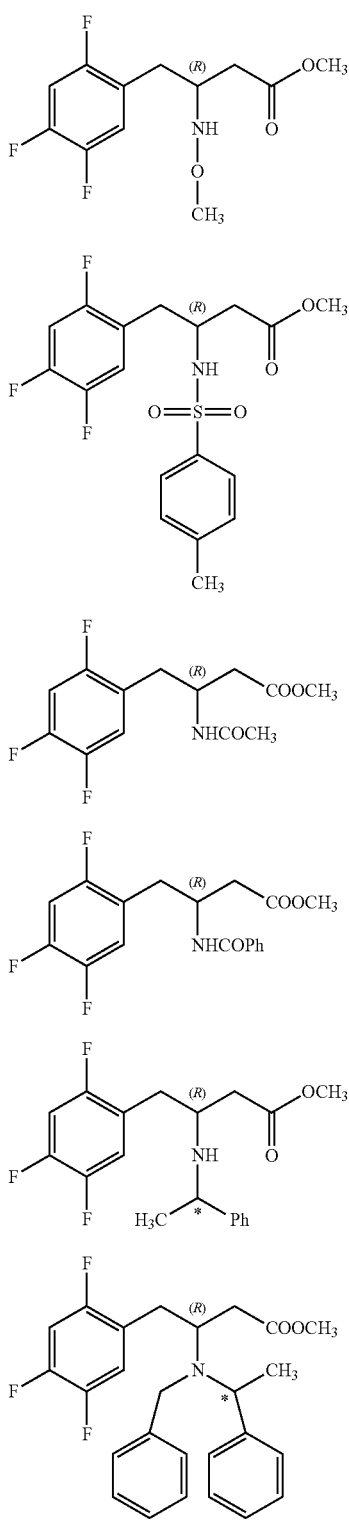

embodiment, the intermediate of formula II is provided as a mixture of the Z-isomer and the E-isomer.

In the intermediate of formula III, the halides are typically selected from chloride, bromide and iodide, and are particularly chloride.

In preferred embodiment, in step (b) the borating agent is selected from optionally chiral boronic esters, optionally chiral alkyl boranes, and optionally alkyl-aryl boranes. Typically, the boronic ester is selected from bis(pinacolato)diboron, bis(catecholato)diboron, bis(neopentyl-glycolato)diboron, bis(hexylene-glycolato)diboron, pinacolborane, and catecholborane. Typically, the alkyl borane is selected from (S)-bis(pinene)borane, (R)-bis(pinene)borane and bis(terpenoyl)borane. The alkyl-aryl borane is typically selected from 2-methyl-5-phenylborolane and 2,5-diphenylborolane.

Typically, in step (b) the borating agent is present in an amount of 1.05-1.5 equivalents, particularly of 1.1-1.3 equivalents, with respect to the intermediate of formula II.

According to one aspect, step (b) is a transition metal catalyzed process, particularly a transition metal catalyzed process using a catalyst comprising a transition metal compound. The transition metal compound is typically selected from copper(I) chloride, copper(II) bromide, copper(I) iodide, copper(I) oxide, copper(II) oxide, copper(I) acetate, copper(II) triflate, copper(II) carbonate, and any combination thereof. Typically, the transition metal compound is present in an amount of 1-15 mol %, particularly of 2-12 mol %, and more particularly 4-10 mol % to the intermediate of formula II.

In asymmetric approach offers the advantage that inexpensive and simple transition metal compounds as for example copper(I) chloride or copper(II) carbonate can be used preferably as metal catalyst.

In the transition metal catalyzed process of step (b), the suitable solvent is typically selected from tetrahydrofuran (THF), dimethylformamide (DMF), toluene, MeOH, water, 2-methyltetrahydrofuran, and any combination thereof.

The transition metal catalyzed process of step (b) is preferably carried out using copper(II) carbonate in water. Typically, when the transition metal compound is copper(II) carbonate the transition metal catalyzed process is carried out in the absence of a base and the copper(II) carbonate is present in an amount of 5-20 mol %. This approach offers the advantage that inexpensive and simple transition metal compounds in environment friendly solvents, such as water, can be used. Most preferably the transition metal catalyzed process of step (b) is preferably carried out using copper(II) carbonate in water in the presence of an chiral ligand to provide high enantioselectivities.

According to one aspect, step (b) is a transition metal catalyzed process using a catalyst comprising a transition metal compound and at least one ligand. At least one ligand is typically selected from monophosphine ligands, diphosphine ligands, N,O-containing ligand, and any combination thereof. The monophosphine ligand is typically selected from triphenylphosphine, tributylphosphine trimethylphosphine, tricyclohexylphosphine, tri-(o-tolyl)-phosphine, tri-(2-furyl) phosphine, tris(dimethylamino)-phosphine, tribenzylphosphine, tripyrolydinophosphine, tris(4-methoxyphenyl)phosphine and any combination thereof. The diphosphine ligand is typically selected from 1,2-bis(diphenyl-phosphino)benzene, 1,1,-bis(di-tert-butylphosphino)ferrocene, (oxydi-2,1-phenylene)bis-(diphenylphosphine), and any combination thereof. The N,O-containing ligand is preferably D-glucozamine.

In a particularly preferred embodiment, the intermediate of formula II in step (a) is provided by a process as defined below.

In one embodiment, the intermediate of formula II is provided as the E-isomer. In another embodiment, the intermediate of formula II is provided as the Z-isomer. In a further Typically, the at least one ligand is present in an amount of 1-15 mol %, particularly of 2-12 mol %, and more particularly 4-10 mol %, with respect to the intermediate of formula II.

Preferably, the ligand is chiral and selected from (R)-2,2'-bis(diphenylphosphino)-1,1-binaphthalene, (S)-2,2'-bis(diphenylphosphino)-1,1-binaphthalene, (S,R)-(diphenylphosphino)-ferrocenyl-ethyldi-tert-butylphosphine, (R,S)-(diphenylphosphino)-ferrocenyl-ethyldi-tert-butylphosphine, (S)-1-($S_p$)-2-[2-(diphenylphosphino)-phenyl]-ferrocenyl-ethylbis[3,5-bis(trifluoromethyl)phenyl]phosphine, (R)-1-($R_p$)-2-[2-(diphenylphosphino)-phenyl]-ferrocenyl-ethylbis[3,5-bis(trifluoromethyl)phenyl]phosphine, (S)-4-tert-butyl-2-[($S_p$)-2-(diphenylphosphino)ferrocenyl]-2-oxazoline, (R)-4-tert-butyl-2-[($S_p$)-2-(diphenylphosphino)ferrocenyl]-2-oxazoline, (1S,1'S)-1,1'-bis[bis[3,5-bis(trifluoromethyl)phenyl]phosphino]-2,2'-bis[(S)-dimethylamino)phenylmethyl], (1R,1'R)-1,1'-bis[bis[3,5-bis(trifluoromethyl)phenyl]phosphino]-2,2'-bis[(R)-(dimethylamino)phenylmethyl], and any combination thereof, and is particularly (R)-2,2'-bis(diphenylphosphino)-1,1-binaphthalene, (S)-2,2'-bis(diphenylphosphino)-1,1-binaphthalene, and (S)-1-($S_p$)-2-[2-(diphenylphosphino)-phenyl]-ferrocenyl-ethylbis[3,5-bis(trifluoromethyl)phenyl]phosphine, (R)-1-($R_p$)-2-[2-(diphenylphosphino)-phenyl]-ferrocenyl-ethylbis[3,5-bis(trifluoromethyl)phenyl]phosphine.

According to another aspect, the transition metal catalyzed process of step (b) is carried out in the presence of a base, particularly wherein the base is selected from NaOt-Bu, KOt-Bu, $K_2CO_3$, $MgCO_3$, $Na_2CO_3$, $Na_3PO_4$, $K_3PO_4$, KOAc, NaOAc, and any combination thereof, more particularly NaOt-Bu. The base is typically present in an amount of 52-25 mol %, particularly of 4-20 mol %, and more particularly 6-15 mol %, with respect to the intermediate of formula II.

The transition metal catalyzed process of step (b) is typically is carried out at a temperature of 15° C. to 30° C., particularly from 20° C. to 25° C., and more particularly room temperature.

According to another aspect, step (b) is a transition metal free catalyzed process, particularly a transition metal free catalyzed process using a base and at least one ligand. The base is typically selected from cesium carbonate, cesium phosphate, cesium hydroxide, cesium chloride, cesium fluoride, cesium iodide, and any combination thereof, but particularly cesium carbonate. Typically, the base is present in an amount of 5-40 mol %, particularly of 8-30 mol %, and more particularly 10-20 mol % to the intermediate of formula II.

The at least one ligand of the transition metal free catalyzed process of step (b) is selected from monophosphine ligands, diphosphine ligands, and any combination thereof. The monophosphine ligand is typically selected from triphenylphosphine, trimethylphosphine, tricyclohexylphosphine, tri-(o-tolyl)-phosphine, tri-(2-furyl)phosphine, tris(dimethylamino)-phosphine, tribenzylphosphine, tripyrolydinophosphine, tris(4-methoxyphenyl)phosphine and any combination thereof. The diphosphine ligand is typically selected from 1,2-bis(diphenyl-phosphino)benzene, 1,1,-bis(di-tert-butylphosphino)ferrocene, (oxydi-2,1-phenylene)bis-(diphenylphosphine), and any combination thereof. Typically, the at least one ligand is present in an amount of 3-25 mol %, particularly of 5-20 mol %, and more particularly 8-15 mol %, with respect to the intermediate of formula II.

Preferably, the ligand is chiral and selected from (R)-2,2'-bis(diphenylphosphino)-1,1-binaphthalene, (S)-2,2'-bis(diphenylphosphino)-1,1-binaphthalene, (S,R)-(diphenylphosphino)-ferrocenyl-ethyldi-tert-butylphosphine, (R,S)-(diphenylphosphino)-ferrocenyl-ethyldi-tert-butylphosphine,(S)-1-($S_p$)-2-[2-(diphenylphosphino)-phenyl]-ferrocenyl-ethylbis[3,5-bis(trifluoromethyl)phenyl]phosphine, (R)-1-($R_p$)-2-[2-(diphenylphosphino)-phenyl]-ferrocenyl-ethylbis[3,5-bis(trifluoromethyl)phenyl]phosphine, (S)-4-tert-butyl-2-[($S_p$)-2-(diphenylphosphino)ferrocenyl]-2-oxazoline, (R)-4-tert-butyl-2-[($S_p$)-2-(diphenylphosphino)ferrocenyl]-2-oxazoline, (1S,1'S)-1,1'-bis[bis[3,5-bis(trifluoromethyl)phenyl]phosphino]-2,2'-bis[(S)-dimethylamino)phenylmethyl], (1R,1'R)-1,1'-bis[bis[3,5-bis(trifluoromethyl)phenyl]phosphino]-2,2'-bis[(R)-(dimethylamino)phenylmethyl], and any combination thereof, and is particularly (R)-2,2'-bis(diphenylphosphino)-1,1-binaphthalene, (S)-2,2'-bis(diphenylphosphino)-1,1-binaphthalene, and (S)-1-($S_p$)-2-[2-(diphenylphosphino)-phenyl]-ferrocenyl-ethylbis[3,5-bis(trifluoromethyl)phenyl]phosphine, (R)-1-($R_p$)-2-[2-(diphenylphosphino)-phenyl]-ferrocenyl-ethylbis[3,5-bis(trifluoromethyl)phenyl]phosphine.

In the transition metal free catalyzed process of step (b), the suitable solvent is typically selected from tetrahydrofuran (THF), dimethylformamide (DMF), toluene, MeOH, water, 2-methyltetrahydrofuran, and any combination thereof, and is particularly THF.

The transition metal free process of step (b) is typically is carried out at a temperature of 25° C. to 80° C., particularly from 30° C. to 70° C., and more particularly about 60° C.

In one embodiment, the intermediate of formula III is obtained in step (b) as the (R)-isomer. In another embodiment, the intermediate of formula III is obtained in step (b) as a mixture of the (R)-isomer and the (S)-isomer. Typically, the (S)-isomer and the (R)-isomer of the intermediate of formula III are separated before step (c).

In a particularly preferred embodiment, step (c) is typically carried out with retention of configuration provided in step (b). Therefore, the obtained (R)-isomer of the intermediate of formula (III) in step (b) in converted to the corresponding (R)-isomer of the intermediate of formula (I).

According to another aspect, in step (c) the intermediate of formula III is converted to the intermediate of formula I by an amination process.

In a preferred embodiment, the amination process in step (c) comprises or consists the steps of:
(c1) reacting the intermediate of formula III with an organo-zinc compound and/or an organo-magnesium compound in a suitable solvent, and
(c2) reacting with an electrophilic aminating reagent in a suitable solvent.

Typically, in step (c1) the organo-zinc compound is selected from the group consisting of zinc compounds with two alkyl residues, wherein the alkyl residues having from 1 to 12 carbon atoms, and wherein the organo-zinc compound is particularly diethylzinc, dimethylzinc, methylzinc chloride, ethylzinc chloride or any combination thereof. The organo-zinc compound typically present in an amount of 1.0 to 2.0 equivalents, particularly of 1.05 to 1.2 equivalents, and more particularly about 1.1 equivalents, with respect to the compound of formula III.

When in step (c1) the organo-magnesium compound is used, it is typically selected from the group consisting of cyclpropylmagnesium chloride, cyclohexylmagnesium chloride isopropylmagnesium chloride, particularly ethylmagnesium chloride and methylmagnesium chloride, and any combination thereof. The organo-magnesium compound is typically present in an amount of 2.0 to 2.5 equivalents, particularly of 2.1 to 2.3 equivalents, and more particularly about 2.2 equivalents, with respect to the compound of formula III.

In step (c1) the suitable solvent is typically selected from aprotic solvents. The suitable solvent is typically selected from THF, toluene, hexane, heptane, diglyme, 2-methyltetrahydrofuran, and any combination thereof, and is particularly THF.

Step (c1) is typically carried out at a temperature of −15° C. to 25° C., particularly from −5° C. to 5° C., and more particularly 0° C.

Typically, in step (c2) the electrophilic aminating reagent is selected such that the corresponding intermediate of formula I is obtained with $R^4$ and $R^5$ as defined above. Typically, the electrophilic aminating reagent is selected from the group consisting of monochloramine, hydroxylamine-O-sulfonicacid, N-chloro tosylamide sodium salt, benzylchloroamine, phenylethanechloroamine, O-mesitylenesulphonyl-hydroxylamine, N-α-methybenzylchloroamine, O-benzyl-N-chlorohydroxylamine, N-benzyl-1-phenylethylchloramine, and any combination thereof. The electrophilic aminating reagent is typically present in an amount of more than 1 equivalent, particularly of 2.0 to 3.5 equivalents, more particularly of 2.1 to 3.4 equivalents, and most particularly of 2.2 to 3.2 equivalents, with respect to the intermediate of formula III.

This economic approach offers the advantage that inexpensive, simple and commercially available aminating reagents or their precursors can be used.

In step (c2) the suitable solvent is typically selected from aprotic solvents. The suitable solvent is typically selected from THF, toluene, hexane, heptane, diglyme, 2-methyltetrahydrofuran, and any combination thereof, and is particularly THF.

Step (c2) is typically carried out at a temperature of 20° C. to 30° C., particularly from 20° C. to 25° C., and more particularly at room temperature.

In another preferred embodiment, the amination process in step (c) comprises or consists the steps of:
(c3) reacting the intermediate of formula III with a haloboron agent and/or a bifluoride agent, and
(c4) reacting with an azide aminating reagent.

Typically, in step (c3), the halo-boron agent is selected from boron trichloride, boron triiodide, and boron tribromide, and any combination thereof, and is particularly boron trichloride.

When in step (c3) the bifluoride agent is used, it is typically selected from potassium hydrogen bifluoride, ammonium hydrogen bifluoride, sodium hydrogen bifluoride, and any combination thereof, and is particularly potassium hydrogen bifluoride.

Typically, in step (c4) the azide aminating reagent is selected such that the corresponding intermediate of formula I is obtained with $R^4$ and $R^5$ as defined above. Typically, the azide aminating reagent is selected from the group consisting of alkyl azides and aryl azides, each having the formula VIIIa or VIIIb

 $R^4N_3$ (VIIIa)

 $R^5N_3$ (VIIIb)

with $R^4$ and $R^5$ being as defined for formula I.

Particularly, the azide aminating agent is selected from benzyl azide, tosylazide, benzoylazide, and acetylazide.

In a further preferred embodiment, step (c) comprises or consists the steps of:
(c5) reacting the intermediate of formula III with an oxidation agent in a suitable solvent to obtain the intermediate of formula IV

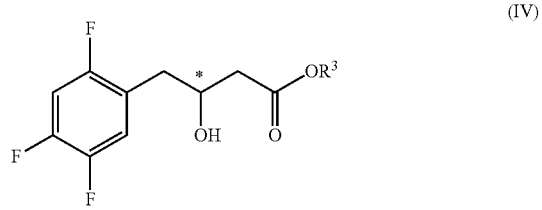

(IV)

wherein the stereogenic center marked with an * is either in (R)- or (S)-configuration at marked center, or it is in racemic form, and
wherein $R^3$ is selected from alkyl residues having from 1 to 6 carbon atoms;
(c6) reacting the intermediate of formula IV with an aminating agent to obtain an intermediate of formula I.

Typically, in step (c5), the oxidation agent is selected from the group consisting of sodium perborate hydrate, hydrogen peroxide, sodium hypochlorite, sodium percarbonate, sodium bromate, potassium bromate, sodium chlorate, potassium chlorate, oxone, and any combination thereof. The oxidation agent is typically present in an amount of 1.0 to 5.5 equivalents, particularly of 1.8 to 5.0 equivalents, and more particularly of 2.0 to 4.0 equivalents, with respect to the intermediate of formula III.

This environmentally friendly approach offers the advantage that simple, inexpensive and waste-free oxidizing agents can be used. This approach offers the further advantage that a one-pot protocol from intermediate of formula II over intermediate of formula III to intermediate of formula IV can be used. This approach also offers the retention of configuration provided in step (b).

In step (c5) the suitable solvent is typically selected from THF, water, methanol, acetonitrile, ethylacetate, isopropylacetate, ethanol, propanole, 2-methyltetrahydrofuran, and any combination thereof.

Step (c5) is typically carried out at a temperature of 15° C. to 30° C., particularly from 20° C. to 25° C., and more particularly at room temperature.

In step (c6) the aminating agent is typically selected such that the corresponding intermediate of formula I is obtained with $R^4$ and $R^5$ as defined above. Typically, the aminating reagent is selected from the group consisting of ammonia, alkyl amines, aryl amines, and aryl-alkyl amines, each having the formula IX

 $R^4R^5NH$ (IX)

with $R^4$ and $R^5$ being as defined for formula I; or in step (c6') using alkyl nitriles, and aryl nitriles, each having the formula Xa or Xb

 $R^4CN$ (Xa)

 $R^5CN$ (Xb)

with $R^4$ and $R^5$ being as defined for formula I; and any combination thereof.

Particularly, the amine used as aminating agent in step (c6) is selected from benzylamine, p-methoxyaniline, 3,4-dimethoxybenzylamine, O-benzyl-hydroxylamine, O-methyl-hydroxylamine, tosylamine, dimethylamine, dibenzylamine, N-α-methylbenzylamine, N-benzyl-1-phenylethylamine, N-bis-[α-methylbenzyl]. Particularly the nitrile used as aminating agents in step (c6) is selected from acetonitrile, benzonitrile, chloroacetonitrile, phenylacetonitrile, acrylonitrile, isopropylnitrile, 2-methylbutyronitrile, mandelonitrile, and 2-methoxy-2-phenylacetonitrile.

When in step (c6) the aminating agent is selected from ammonia, alkyl amines, aryl amines, and aryl-alkyl amines, it is typically present in an amount of 1.0 to 3 equivalents, and particularly about 1.0 to 2.0 equivalent, with respect to the intermediate of formula IV.

When in step (c6') the aminating agent is selected alkyl nitriles, and aryl nitriles, it is typically present in an amount of 2.5 to 10 equivalents, particularly of 4 to 8 equivalents, and more particularly about 5 to 7.5 equivalents with respect to the intermediate of formula IV.

In a particularly preferred embodiment, step (c6) is a transition metal catalyzed process, particularly a transition metal catalyzed process using a catalyst comprising a transition metal compound and optionally at least one ligand, particularly when the aminating agent is selected from ammonia, alkyl amines, aryl amines, and aryl-alkyl amines.

In the transition metal catalyzed process of step (c6), the transition metal compound is selected from a gold compound, particularly Au/TiO$_2$; a rhodium compound, particularly Cp*RhCl$_2$dimer; an iron compound, particularly FeBr$_3$, FeCl$_3$; an iridium compound, particularly IrCl(cod)$_2$dimer, Cp*IrCl$_2$dimer, Cp*IrBr$_2$dimer or Cp*IrI$_2$dimer; and a ruthenium compound, particularly Ru(p-cymene)Cl$_2$dimer, Ru(p-cymene)Cl$_2$dimer, Ru(p-cymene)Cl$_2$dimer or Ru$_3$CO$_{12}$. The transition metal compound is typically present in an amount of 1-15 mol %, particularly of 2-7.5 mol %, and more particularly 3.5-5.5 mol %, to the intermediate of formula IV.

This approach offers the advantage that commercially available transition metal compounds or active catalysts can be used.

In the transition metal catalyzed process of step (c6), the optionally at least one ligand is typically selected from monophosphine ligands, diphosphine ligands, amine type ligands, and any combination thereof. Typically, the monophosphine ligand is typically selected from triphenylphosphine, tributylphosphine 2-dicyclohexylphosphino-1-phenyl-1H-pyrole, trimethylphosphine, neomethyldiphenylphosphine, tricyclohexylphosphine and any combination thereof. The diphosphine ligand is typically selected 1,2-bis(diphenylphosphino)benzene, 1,1,-bis(di-tert-butylphosphino)ferrocene, (oxydi-2,1-phenylene)bis-(diphenylphosphine), (R)-2,2-bis(diphenylphosphino)-1,1-binaphthalene, (S)-2,2-bis(diphenylphosphino)-1,1-binaphthale, (S,R)-(diphenylphosphino)-ferrocenyl-ethyldi-tert-butylphosphin, (R,S)-(diphenylphosphino)-ferrocenyl-ethyldi-tert-butylphosphin, 1,3-bis(diphenylphosphino)propane, 2,2-bis(diphenylphosphino)-1,1-binaphthyl, and any combination thereof. The amine type ligand may be an amino acid. Typically, the amine type ligand is selected from (D)-pyroglutamic acid, (L)-pyroglutamic acid, (D)-proline intermediates, (L)-proline intermediates, (D)-methyl-N-phenylcarbamate, (L)-methyl-N-phenylcarbamate, (D)-N-phthaloylglycine, (L)-N-phthaloylglycine, (D)-glutamic acid, and (L)-glutamic acid. Typically, the at least one ligand is present in an in an amount of 1-15 mol %, particularly of 2-7.5 mol %, and more particularly 3.5-5.5 mol %, to the intermediate of formula IV.

The transition metal catalyzed process of step (c6) is optionally carried out in the presence of a base, particularly wherein the base is selected from NaHCO$_3$, KHCO$_3$, KOH, NaOH, NaOt-Bu, KOt-Bu, K$_3$PO$_4$, and any combination thereof, more particularly NaHCO$_3$. The base is typically present in an amount of 1-15 mol %, particularly of 3-12 mol %, and more particularly 5-10 mol %, with respect to the intermediate of formula II.

In a further particularly preferred embodiment, step (c6') is an acid catalyzed process. Typically, the acid is selected from Brønsted acids, and is particularly trifluoromethanesulfonic acid (HOTf), methanesulfonic acid, p-toluenesulfonic acid (PTSA), chlorosulfonic acid, 2,5-dinitrobenzenesulfonic acid (DNBSA), sulfuric acid or dodecylbenzenesulfonic acid (DBSA), and is most particularly HOTf. The acid is typically present in an amount of 0.15-15 equivalents, particularly of 1-10 equivalents, and more particularly 5-7.5 equivalents, to the intermediate of formula IV.

In a particularly preferred embodiment, steps (c5) and (c6) are carried out with retention of configuration provided in step (b). Particularly, the obtained (R)-isomer of the intermediate of formula III in step (b) is converted to the corresponding (R)-isomer of the intermediate of formula IV in step (c5). Particularly, the obtained (R)-isomer of the intermediate of formula IV is then converted to the corresponding (R)-isomer of the intermediate of formula I in step (c6).

In a particularly preferred embodiment in the process to obtain the intermediate of formula I, R$^4$ and R$^5$ are hydrogen and the process comprises or consists the steps of:
(a) providing an intermediate of formula II, preferably by a process as defined below,

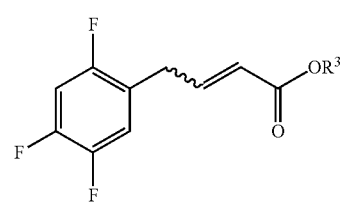

(b) reacting the intermediate of formula II with
a. bis(pinacolato)diboron, preferably present in an amount of 1.1-1.3 equivalents, more preferably about 1.1 equivalents,
b. in the presence of copper(I) chloride, preferably present in an amount of 4-12 mol %, more preferably about 10 mol %;
c. mono- and/or diphosphine ligands, preferably present in an amount of 4-12 mol %, more preferably 8-10 mol %, and
d. optionally NaOt-Bu, preferably present in an amount of 10-20 mol %, more preferably about 15 mol %,
each to the intermediate of formula II, in THF at a temperature of 20° C. to 25° C., preferably at room temperature,
to obtain an intermediate of formula III,

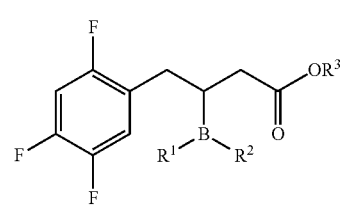

wherein $R^1$ and $R^2$ form a pinacolato group and $R^3$ is selected from alkyl residues having from 1 to 6 carbon atoms;

(c) reacting the intermediate of formula III with e. methylmagnesium chloride, preferably present in an amount of 1.8 to 2.3 equivalents, more preferably about 2.0 equivalents, with respect to the intermediate of formula III, in THF at a temperature of −3° C. to 3° C., preferably at about 0° C.; and with f. monochloramine chloride, preferably present in an amount of 2.0 to 3.5 equivalents, more preferably about 3.2 equivalents, and/or g. hydroxylamine-O-sulfonic acid chloride, preferably present in an amount of 2.0 to 3.5 equivalents, more preferably about 2.2 equivalents, each with respect to the intermediate of formula III, in THF and water at a temperature of 20° C. to 25° C., preferably at room temperature, to obtain the intermediate of formula I.

In another particularly preferred embodiment in the process to obtain the intermediate of formula I, $R^4$ and $R^5$ are different, and are independently selected from (i) hydrogen;
(ii) alkyl residues optionally chiral, having from 1 to 12 carbon atoms, wherein the alkyl residues are optionally aryl and/or aryloxy substituted;
(iii) alkyloxy residues optionally chiral, having from 1 to 12 carbon atoms, wherein the alkyloxy residues are optionally aryl substituted;
(iv) aryl residues optionally chiral, having from 6 to 24 carbon atoms, wherein the aryl residues are optionally alkyl and/or alkyloxy substituted;
(v) aryloxy residues optionally chiral, having from 6 to 24 carbon atoms, wherein the aryloxy residues are optionally alkyl substituted;
(vi) benzyl;
(vii) alkaloyl residues optionally chiral, having from 2 to 13 carbon atoms, wherein the alkaloyl residues are optionally aryl substituted;
(viii) aroyl residues optionally chiral, having from 7 to 25 carbon atoms, wherein the aryloxy residues are optionally alkyl substituted; and
(ix) alkoxycarbonyl residues optionally chiral, having from 2 to 13 carbon atoms;
(x) aryloxycarbonyl residues optionally chiral, having from 7 to 25 carbon atoms; and
(xi) tosyl;

and particularly $R^4$ is hydrogen and $R^5$ is tosyl, or $R^4$ is hydrogen and $R^5$ is tosyl, or, $R^4$ is hydrogen and $R^5$ is benzyl, or $R^4$ is hydrogen and $R^5$ is O-benzyl, or $R^4$ is hydrogen and $R^5$ is O-methyl, or $R^4$ is benzyl and $R^5$ is N-α-methylbenzyl, or $R^4$ is hydrogen and $R^5$ is tert-butyl-oxy-carbonyl, or $R^4$ is hydrogen and $R^5$ is benzyl-oxy-carbonyl, or $R^4$ is hydrogen and $R^5$ is benzoyl, or $R^4$ is hydrogen and $R^5$ is acetyl, or $R^4$ is hydrogen and $R^5$ is N-α-methylbenzyl, or $R^4$ is hydrogen and $R^5$ is phenyl-O-methyl;

the process comprises or consists the steps of:

(a) providing an intermediate of formula II, preferably by a process as defined below,

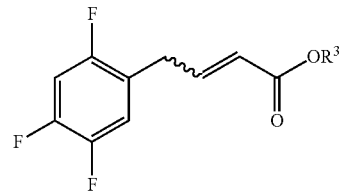

(II)

(b) reacting the intermediate of formula II with (i) bis(pinacolato)diboron, preferably present in an amount of 1.1-1.3 equivalents, more preferably about 1.1 equivalents,
(ii) in the presence of copper(I) chloride, preferably present in an amount of 4-12 mol %, more preferably about 10 mol %;
(iii) mono- and/or diphosphine ligands, preferably present in an amount of 4-12 mol %, more preferably 8-10 mol %, and
(iv) optionally NaOt-Bu, preferably present in an amount of 10-20 mol %, more preferably about 15 mol %, each with respect to the intermediate of formula II, in THF at a temperature of 20° C. to 25° C., preferably at room temperature, to obtain an intermediate of formula III,

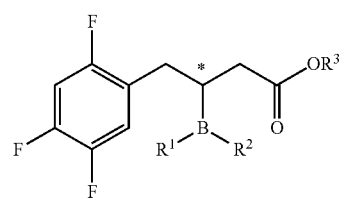

(III)

wherein the stereogenic center marked with an * is either in (R)- or (S)-configuration at marked center, or it is in racemic form, and wherein $R^1$ and $R^2$ form a pinacolato group and $R^3$ is selected from alkyl residues having from 1 to 6 carbon atoms;

(c) reacting the intermediate of formula III with (i) sodium perborate hydrate, preferably present in an amount of 1.8 to 5.0 equivalents, more preferably about 4.0 equivalents, with respect to the intermediate of formula III in THF and water, and/or
(ii) aqueous hydrogen peroxide, preferably present in an amount of 1.8 to 5.0 equivalents, more preferably about 2.0 equivalents, with respect to the intermediate of formula III in THF and water, and/or
(iii) sodium hypochlorite in an aqueous solution, preferably present in an amount of 1.8 to 5.0 equivalents, more preferably about 1.5 equivalents;

with respect to the intermediate of formula III, in methanol and water, at a temperature of 20° C. to 25° C., preferably at room temperature, to obtain the intermediate of formula IV

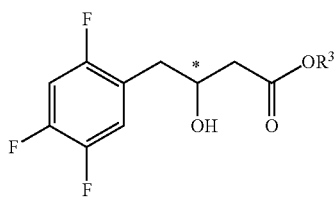

(IV)

wherein the stereogenic center marked with an * is either in (R)- or (S)-configuration at marked center, or it is in racemic form, and (d) reacting the intermediate of formula IV with an aminating agent to obtain an intermediate of formula I.

In particularly preferred embodiment, the intermediate of formula I is an intermediate of formula I', and the isomers, and the isomer mixtures thereof.

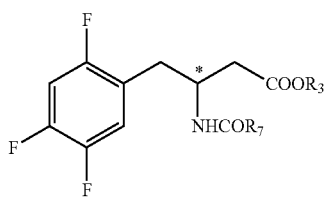

(I')

wherein the stereogenic center marked with an * is either in (R)- or (S)-configuration at marked center, or it is in racemic form and wherein $R^3$ is selected from alkyl residues having from 1 to 6 carbon atoms; and $R^7$ is selected from alkyl residues having from 1 to 6 carbon atoms and aryl residues, having from 6 to 24 carbon atoms, optionally substituted.

In a further aspect, processes for the preparation of an intermediate of formula I starting from an intermediate of formula III as defined above are described.

In a further aspect, processes for the preparation of an intermediate of formula I starting from an intermediate of formula IV obtained or obtainable in a process starting from an intermediate of formula III as defined above are described.

In still further aspect, processes for the preparation of an intermediate of formula III starting from an intermediate of formula II as defined above are described.

The Intermediate of Formula III

The present invention also relates to an intermediate of formula III, and the isomers, and the isomer mixtures thereof,

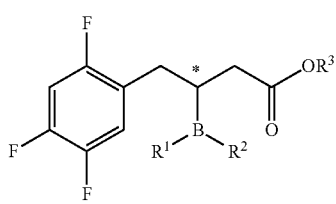

(III)

wherein the stereogenic center marked with an * is either in (R)- or (S)-configuration at marked center, or it is in racemic form, and wherein $R^1$ and $R^2$ are identical or different, and are selected from (i) alkyl or alkoxy residues, each having from 1 to 12 carbon atoms, wherein each alkyl or alkoxy residue is optionally aryl substituted;

(ii) aryl or aryloxy residues, each having from 6 to 14 carbon atoms, wherein each aryl or aryloxy residue is optionally alkyl substituted;

(iii) halides; and (iv) wherein $R^1$ and $R^2$ optionally form a chiral or non-chiral 5 to 10 membered mono or bicyclic ring, wherein the ring is optionally substituted at least one position with an alkyl residue having from 1 to 12 carbon atoms and/or an aryl residue having from 6 to 14 carbon atoms, and wherein $R^1$ and $R^2$ optionally from a O-benzenedioxy residue;

and wherein $R^3$ is selected from alkyl residues having from 1 to 6 carbon atoms.

In a preferred embodiment, the alkyl or alkyloxy residues each have from 1 to 5 carbon atoms, particularly 1 to 3 carbon atoms. In another preferred embodiment, the aryl or aryloxy residues each have from 6, 7 or 14 carbon atoms. The alkyl or alkoxy residues may be aryl substituted. The aryl or aryloxy residues may be alkyl substituted.

In one embodiment, $R^1$ and Reform a 5 to 6 membered ring. In one preferred embodiment, $R^1$ and $R^2$ form a chiral ring. In another preferred embodiment $R^1$ and $R^2$ form a non-chiral ring.

In a further embodiment, $R^1$ and $R^2$ are a halide selected from chloride, bromide and iodide, and are particularly chloride. In still a further embodiment $R^1$ and $R^2$ form a chiral or non-chiral 5 to 10 membered mono or bicyclic ring, wherein the ring is substituted at least one position with an alkyl residue having from 1 to 12 carbon atoms and/or an aryl residue having from 6 to 14 carbon atoms.

Particularly, the isomers of the intermediate of formula III have the formula

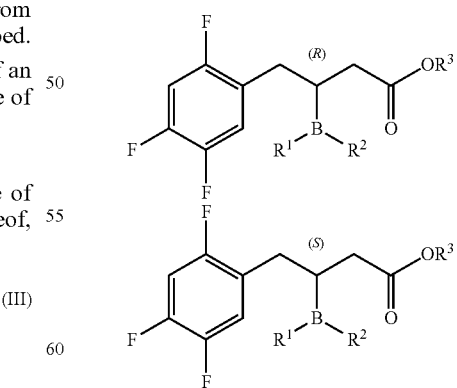

In a particularly preferred embodiment, $R^1$ and $R^2$ from an O-benzenedioxy residue and $R^3$ is selected from alkyl residues having from 1 to 6 carbon atoms. In further particularly preferred embodiments, the intermediate of formula III is

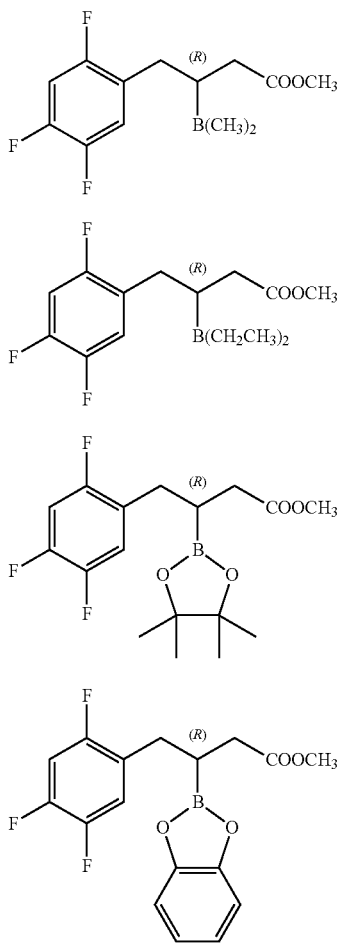

(IIIa)

(IIIb)

(IIIc)

(IIId)

According to another aspect, the intermediate of formula III is obtained or obtainable by a process as defined above.

According to another aspect, there is also provided the use of an intermediate of formula II in a process for the preparation of an intermediate of formula III as defined above.

According to another aspect, there is also provided the use of an intermediate of formula III in a process for the preparation of (R)-4-oxo-4-[3-(trifluoromethyl)-5,6-dihydro[1,2,4]triazolo[4,3-a]pyrazin-7(8H)-yl]-1-(2,4,5-trifluorophenyl)butan-2-amin).

According to another aspect, there is also provided the use of an intermediate of formula III in a process for the preparation of an intermediate of formula I.

According to another aspect, there is also provided the use of an intermediate of formula III in a process for the preparation of an intermediate of formula I, wherein the intermediate of formula I is used in a process for the preparation of (R)-4-oxo-4-[3-(trifluoromethyl)-5,6-dihydro[1,2,4]triazolo [4,3-a]pyrazin-7(8H)-yl]-1-(2,4,5-trifluorophenyl)butan-2-amin).

According to another aspect, there is also provided the use of an intermediate of formula III in a process for the preparation of an intermediate of formula IV.

According to another aspect, there is also provided the use of an intermediate of formula III in a process for the preparation of an intermediate of formula IV, wherein the intermediate of formula IV is used in a process for the preparation of an intermediate of formula I as defined in any of items 1 to 7, wherein the intermediate of formula I is optionally used in a process for the preparation of (R)-4-oxo-4-[3-(trifluoromethyl)-5,6-dihydro[1,2,4]triazolo[4,3-a]pyrazin-7(8H)-yl]-1-(2,4,5-trifluorophenyl)butan-2-amin).

Process for the Preparation of the Intermediate of Formula II

According to a further aspect, there is also provided a process for the preparation of an intermediate of formula II

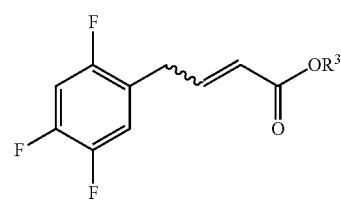

(II)

wherein $R^3$ is selected from alkyl residues having from 1 to 6 carbon atoms;
the process comprises or consists the steps of:
(a) providing an intermediate of formula V

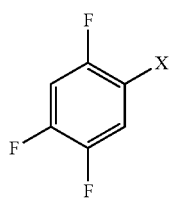

(V)

(b) reacting the intermediate of formula V, wherein X is selected from Cl, Br, I, and is preferably Br with a Grignard compound, or with magnesium in the presence of an activating agent, wherein the activating agent is particularly selected from iodine, methyl iodide, 1,2-dibromoethane, and any combination thereof;
in a suitable solvent to obtain an intermediate of formula VI

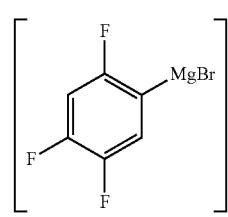

(VI)

(c) reacting the intermediate of formula VI with a compound of formula VII

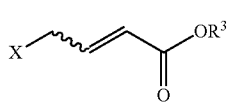

(VII)

wherein X is selected from Cl, Br, and I, and is preferably Br;
wherein $R^3$ is the same as above;
in a metal catalyzed cross-coupling process in a suitable solvent to obtain the intermediate of formula II.

In one embodiment, the intermediate of formula II is obtained as the E-isomer. In another embodiment, the intermediate of formula II is obtained as the Z-isomer. In a further embodiment, the intermediate of formula II is obtained as a mixture of the Z-isomer and the E-isomer. Typically, the Grignard compound has the formula R⁶MgX, wherein X is selected from Cl, Br or I, and particularly wherein R⁶ is an alkyl residue having from 1 to 6 carbon atoms. In a preferred embodiment, the Grignard compound is selected from the group consisting of i-PrMgCl, MeMgCl, s-BuMgCl, i-PrMgCl.LiCl complex, s-BuMgCl.LiCl complex, and any combination thereof, and is particularly i-PrMgCl. Typically, the Grignard compound is present in an amount of 1.1 to 1.5 equivalents, particularly of 1.2-1.3 equivalents and more particularly about 1.2 equivalents, with respect to the compound of formula V. Typically, if the intermediate of formula VI is prepared using magnesium, the magnesium is activated using catalytic amounts, particularly 0.10-10 mol %, of an activating agent with respect to the intermediate of formula V.

In a preferred embodiment the activating agent is selected from iodine, methyl iodide, 1,2-dibromoethane, and any combination thereof.

Typically, in step (b) the suitable solvent is selected from THF, toluene, methyl-tert-butylether, diethylether, 2-methyltetrahydrofuran, and any combination thereof, and is particularly THF. Particularly, the suitable solvent is preferably substantially water-free.

The reaction with a Grignard compound of step (b) is typically carried out at a temperature of −30° C. to −15° C., particularly of −25° C. to −18° C. and more particularly about −20° C.

In step (c) the metal catalyzed cross-coupling process is typically carried out using a catalyst comprising a metal compound, wherein the metal compound is preferably selected from a cobalt(II) compound, a cobalt(III) compound, an iron (III) compound, iron(II) compound and a manganese(II) compound. In a preferred embodiment, the metal compound is selected from cobalt(II) bromide, iron(III) acetylacetonate, iron(II) acetyacetonate cobalt(III) acetylacetonate, cobalt(II) acetyacetonate and manganese(II) acetylacetonate. Typically, the metal compound is present in an amount of 2-25 mol %, particularly of 4-20 mol % and more particularly 7-15 mol %, with respect to the intermediate of formula VII.

In a preferred embodiment in step (c) the metal catalyzed cross-coupling process is carried out in the presence of an additive. The additive is typically selected from tetramethylethylenediamine (TMEDA), hexamethylenetetramin (HMTA), 1,2-dimethoxyethane, DABCO, and any combination thereof. Typically, the additive in step (c) is present in an amount of 2-40 mol %, particularly of 3-35 mol %, and more particularly 5-30 mol %, with respect to the intermediate of formula VII.

In the metal catalyzed cross-coupling process of step (c) the suitable solvent is typically selected from aprotic solvents. Typically, the suitable solvent is selected from THF, diethylether, 2-methyltetrahydrofuran, methyl-tert-butylether, and any combination thereof.

The metal catalyzed cross-coupling process in step (c) is typically carried out at a temperature of −50° C. to −15° C., particularly from −30° C. to −15° C., and more particularly about −25° C.

In a preferred embodiment, the process comprising or consisting the steps of (a) providing an intermediate of formula V

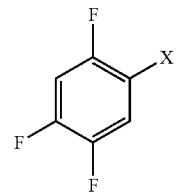

(V)

(b) reacting the intermediate of formula V, wherein X is selected from Cl, Br, I, and is preferably Br with i-PrMgCl, preferably present in an amount of 1.1 to 1.5 equivalents, more preferably about 1.2 equivalents, with respect to the intermediate of formula I in THF at a temperature of −5° C. to −15° C., particularly from −30° C. to −15° C., and more particularly about −25° C.,

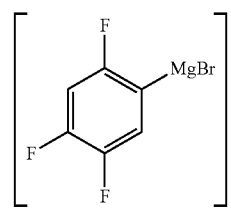

(VI)

(c) reacting the intermediate of formula VI with a compound of formula VIIa

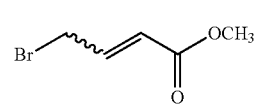

(VIIa)

in the presence of (i) cobalt(II) bromide, preferably present in an amount of 4-12 mol %, more preferably about 6 mol %, or (ii) iron(III)acetylacetonate, preferably present in an amount of 4-12 mol %, more preferably about 10 mol %, and most preferably about 15 mol %

(iii) optionally TMEDA, preferably present in an amount of 5-35 mol %, more preferably 15-30 mol %, and (iv) optionally HMTA, preferably present in an amount of 8-25 mol %, more preferably about 15 mol %, each with respect to the intermediate of formula VIIIa in THF at a temperature of −25° C. to −18° C., preferably at −20° C., to obtain the intermediate of formula II.

The invention will be more fully understood by references to the following examples. They should not, however, be construed as limiting the scope of the invention. The disclosure of all literature and patent citations mentioned herein are expressly incorporated by reference.

EXAMPLES

Example 1a

Synthesis of (E)-methyl-4-(2,4,5-trifluorophenyl)-but-2-enoate (IIa) Through Grignard Exchange Reaction Followed by Iron Catalyzed Cross-Coupling Process A dry and nitrogen-flushed 50 mL flask equipped with a magnetic stirrer and a rubber septum was charged with anhydrous THF (7 mL) and cooled to −20° C. Afterwards 2,4,5-trifluorobenzene (V) (22.2 mmol, 2.6 mL) was initiated through a septum following by slow addition of i-PrMgCl (2 M in THF, 1.20 equiv. according to (V), 13.3 mL). The slightly exothermic reaction occurred and reaction temperature rose to −10° C.

The reaction mixture was stirred for 2.5 hours, until the Br/Mg exchange reaction took place and (VI) was formed.

Into other three-necked dry flask flushed with nitrogen, were placed Fe(acac)$_3$ (2.05 mmol, 10 mol % according to (V), 730 mg), TMEDA (4.1 mmol, 18 mol %, 620 μL) and hexamethylenetetramine (10 mol %, 287 mg). Anhydrous THF (15 mL) was added, the reaction mixture was cooled to 0° C. and vigorously stirred. Afterwards methyl-trans-4-bromo-2-butenoate (VIIa) (17 mmol, 2 mL, 90% purity) was initiated through a rubber septum and reaction mixture was stirred for 30 min. In a such prepared reaction mixture, finally freshly prepared THF solution of Grignard reagent (VI), previously cooled to −20° C., was slowly added (cannulation technique) and reaction mixture was stirred at 0° C. for 2 hours. The reaction mixture was then quenched with saturated aqueous NH$_4$Cl solution (50 mL) and extracted with four portions of MTBE (200 mL). The combined organic phases were washed with brine (100 mL), dried then over anhydrous Na$_2$SO$_4$ and concentrated in vacuo. The crude product was purified with column chromatography (Isolera, gradient elution n-hexane/ethyacetate=1/10) to afford colorless oil (IIa) (1.92 g, 49% yield) as determined with $^1$H, $^{13}$C NMR and MS analysis.

$^1$H NMR (500 MHz, CDCl$_3$, ppm) δ 6.90-7.05 (m, 3H), 5.80 (dt, J=15.5 Hz, 1H), 3.73 (s, 3H), 3.50 (d, J=6.6 Hz, 2H).

$^{13}$C NMR (125 MHz, CDCl$_3$, ppm) δ 30.6, 51.4, 105.5 (dd, J=28.5 Hz, J=21.5 Hz), 118.1 (dd, J=19.0 Hz, J=6.0 Hz), 120.8, (m), 124.5, 145.5, 147.8 (m), 150.1 (m), 156.8 (m), 166.3.

Example 1b

Synthesis of (E)-methyl-4-(2,4,5-trifluorophenyl)-but-2-enoate (IIa) Through Grignard Exchange Reaction Followed by Cobalt Catalyzed Cross-Coupling Process A dry and nitrogen-flushed 200 mL two-necked flask, equipped with a magnetic stirrer and a rubber septum was charged with anhydrous THF (20 mL) and cooled to −20° C. Afterwards 2,4,5-trifluorobenzene (V) (65.2 mmol, 13.7 g, 7.6 mL) was initiated through a septum following by slow addition of i-PrMgCl (2 M in THF, 1.2 equiv. according to (V), 39.6 mL). The reaction temperature was maintained at −10° C. and the reaction mixture was stirred for 3 hours, until Br/Mg exchange reaction was completed and (VI) was formed.

Into a three-necked dry flask flushed with nitrogen, were placed CoBr$_2$ beads (3.76 mmol, 6 mol % according to (V), 822 mg, 99.99% purity), TMEDA (3.76 mmol, 6 mol %, 564 μL) and anhydrous THF (20 mL). Such reaction system was cooled to 0° C. and during intensive stirring methyl-trans-4-bromo-2-butenoate (VIIa) (50 mmol, 8.95 g, 5.98 mL, 90% purity) was initiated through a rubber septum and reaction mixture was stirred for 30 min. Finally, freshly prepared THF solution of Grignard reagent (VI), previously cooled to −20° C., was slowly added and such reaction mixture was intensively stirred at 0° C. for 16 hours. The saturated aqueous NH$_4$Cl solution (150 mL) and extracted with four portions of EtOAc (300 mL). The combined organic phases were washed with brine (200 mL), dried over anhydrous Mg$_2$SO$_4$ and concentrated in vacuo. The crude residue was purified with column chromatography (Isolera; gradient elution n-hexane/EtOAc=1/10) to obtain pure oily product (IIa) (10.8 g, 93% yield) as determined with $^1$H NMR and MS analysis.

Example 1c

Synthesis of (E)-methyl-4-(2,4,5-trifluorophenyl)-but-2-enoate (IIa) Through Grignard Exchange Reaction Followed by Co(acac)$_2$ Catalyzed Cross-Coupling Process A dry and nitrogen-flushed 200 mL two-necked flask, equipped with a magnetic stirrer and a rubber septum was charged with anhydrous THF (12.5 mL) and cooled to −20° C. Afterwards 2,4,5-trifluorobenzene (V) (25.35 mmol, 2.96 mL) was initiated through a septum following by slow addition of i-PrMgCl.LiCl complex (1.2 equiv. according to (V), 23.4 mL). The reaction temperature was maintained −10° C. and the reaction mixture was stirred for 1.5 hour, until Br/Mg exchange reaction was completed and (VI) was formed.

Into a three-necked dry flask flushed with nitrogen, were placed catalyst Co(acac)$_2$ (1.40 mmol, 9 mol % according to (V), 360 mg, 99.99% purity), TMEDA (1.40 mmol, 9 mol %, 0.21 mL) and anhydrous THF (15 mL). Such reaction system was cooled to 0° C. and during intensive stirring methyl-trans-4-bromo-2-butenoate (VIIa) (19.44 mmol, 2.30 mL, 90% purity) was initiated through a rubber septum and reaction mixture was stirred for 30-40 min. Finally, freshly prepared THF solution of Grignard reagent (VI), previously cooled to −20° C., was slowly added and such reaction mixture was intensively stirred at 0° C. for few hours. The saturated aqueous NH$_4$Cl solution (60 mL) was added and extracted with four portions of EtOAc (150 mL). The combined organic phases were washed with brine (120 mL), dried over anhydrous Mg$_2$SO$_4$ and concentrated in vacuo. The crude residue was purified with column chromatography (Isolera; gradient elution n-hexane/EtOAc=1/10) to obtain pure oily product (IIa) (2.01 g, 45% yield) as determined with $^1$H NMR and MS analysis.

Example 1d

Synthesis of (E)-methyl-4-(2,4,5-trifluorophenyl)-but-2-enoate (IIa) Through Grignard Exchange Reaction Followed by Co(acac)$_3$ Catalyzed Cross-Coupling Process A dry and nitrogen-flushed 200 mL two-necked flask, equipped with a magnetic stirrer and a rubber septum was charged with anhydrous THF (12.5 mL) and cooled to −20° C. Afterwards 2,4,5-trifluorobenzene (V) (25.35 mmol, 2.96 mL) was initiated through a septum following by slow addition of i-PrMgCl.LiCl complex (1.2 equiv. according to (V), 23.4 mL). The reaction temperature was maintained −10° C.

and the reaction mixture was stirred for an hour, until Br/Mg exchange reaction was completed and (VI) was formed.

Into a three-necked dry flask flushed with nitrogen, were placed Co(acac)$_3$ (1.40 mmol, 9 mol % according to (V), 500 mg, 99.99% purity), TMEDA (1.40 mmol, 9 mol %, 0.21 mL) and anhydrous THF (15 mL). Such reaction system was cooled to 0° C. and during intensive stirring methyl-trans-4-bromo-2-butenoate (VIIa) (19.44 mmol, 2.30 mL, 90% purity) was initiated through a rubber septum and reaction mixture was vigorously stirred for 30-40 min. Finally, freshly prepared THF solution of Grignard reagent (VI), previously cooled to −20° C., was slowly added and such reaction mixture was intensively stirred at 0° C. for few hours. The saturated aqueous NH$_4$Cl solution was added (60 mL) and extracted with four portions of EtOAc (150 mL). The combined organic phases were washed with brine (120 mL), dried over anhydrous Mg$_2$SO$_4$ and concentrated in vacuo. The crude residue was purified with column chromatography (Isolera; gradient elution n-hexane/EtOAc=1/10) to obtain pure oily product (IIa) (2.80 g, 62% yield) as determined with $^1$H NMR and MS analysis.

Example 2a

Copper-Catalyzed Synthesis of Methyl-3-(4,4,5,5-tetramethyl-1,3,2-dioxaborolan-2-yl)-4-(2,4,5-trifluorophenyl)butanoate (IIIc) in the Presence of Monophosphine Ligands In a two-necked round bottom flask were placed CuCl (0.10 mmol, 10.2 mg), NaOt-Bu (0.15 mmol, 14.42 mg) and Ph$_3$P (0.1 mmol, 26.23 mg) under the nitrogen. Afterwards 1.5 mL of anhydrous THF was added and the reaction mixture was stirred (600 rpm) at ambient temperature for 45 min. Than the solution of bis(pinacolato)diboron (1.1 mmol, 280.0 mg, 1.10 equiv.) in 0.5 mL of THF was slowly dropped into the reaction mixture and after 30 min α,β-unsaturated ester (E)-methyl-4-(2,4,5-trifluorophenyl)-but-2-enoate (IIa) (1.0 mmol, 230.6 mg) dissolved in 0.5 mL THF was added. The reaction mixture was stirred at ambient temperature for 30 min and afterwards MeOH (1.25 mL; THF:MeOH=2:1) or H$_2$O (1.25 mL; THF:H$_2$O=2:1) were added. The reaction system was maintained at ambient temperature and stirred for 24 hours. The reaction mixture was concentrated under the reduced pressure, than brine (10 mL) was added and mixture was transferred to a separating funnel.

The aqueous layer was extracted with two portion of EtOAc (2×30 mL). Combined organic layers were washed with brine (30 mL), dried over Na$_2$SO$_4$ and organic solvent was removed under the reduced pressure. The obtained crude brown product was purified with flash chromatography (SiO$_2$; EtOAc) to obtain 310 mg of yellow liquid (86% yield) (IIIc) as determined with $^1$H, $^{11}$B, $^{13}$C NMR and MS analysis.

$^1$H NMR (500 MHz, CDCl$_3$, ppm) δ 7.01-7.05 (m, 1H), 6.80-6.86 (m, 1H), 3.65 (s, 3H), 2.75 (dd, J=15 Hz, J=5 Hz, 1H), 2.61 (dd, J=15 Hz, J=5 Hz, 1H), 2.37 (d, J=10 Hz, 2H), 1.60 (pentet, 1H), 1.20 (m, 12H).

$^{13}$C NMR (125 MHz, CDCl$_3$, ppm) δ 24.5, 28.4, 34.4, 53.3, 83.4, 105.0 (dd, J=28.8 Hz, J=21.3 Hz), 118.5 (dd, J=20.2 Hz, J=6.3 Hz), 124.5 (m), 147.3 (m), 149.4 (m), 156.0 (dd, J=242.5 Hz, J=2.5 Hz), 173.7.

$^{11}$B (160 MHz, CDCl$_3$, ppm) δ 33.6 (bs).

Example 2b

Copper-Catalyzed Synthesis of Methyl-3-(4,4,5,5-tetramethyl-1,3,2-dioxaborolan-2-yl)-4-(2,4,5-trifluorophenyl)butanoate (IIIc) in the Presence of Diphosphine Ligands In a two-necked round bottom flask were placed CuCl (0.1 mmol, 10.2 mg), NaOt-Bu (0.15 mmol, 14.42 mg) and 1,2-diphenylphosphinobenzene (dppbz; 0.1 mmol, 44.6 mg) or 1,1-bis(di-tert-butylphosphino)ferrocene (dtpf; 0.1 mmol, 47.4 mg) under the nitrogen. Afterwards 1.5 mL of anhydrous THF was added and the reaction mixture was stirred (600 rpm) at ambient temperature for 45 min. Than the solution of bis(pinacolato)diboron (1.1 mmol, 280 mg, 1.10 equiv.) in 0.5 mL of THF was slowly dropped into the reaction mixture and after 30 min α,β-unsaturated ester (E)-methyl-4-(2,4,5-trifluorophenyl)-but-2-enoate (IIa) (1.0 mmol, 230.60 mg) dissolved in 0.5 mL THF was added. The reaction mixture was stirred at ambient temperature for 30 min and afterwards MeOH (1.25 mL; THF:MeOH=2:1) were added. The reaction system was maintained at ambient temperature and stirred for 24 hours. The reaction mixture was concentrated under the reduced pressure and then brine (10 mL) was added and mixture was transferred to a separating funnel. The aqueous layer was extracted with CH$_2$Cl$_2$ (2×30 mL). Combined organic layers were washed with brine (30 mL), dried over Na$_2$SO$_4$ and organic solvent was removed under the reduced pressure. The obtained crude product was purified with flash chromatography (SiO$_2$; CH$_2$Cl$_2$) to obtain 295 mg (82% yield) of yellow liquid (IIIc) as determined with $^1$H, $^{11}$B, $^{13}$C NMR and MS analysis. The conversion of starting material (IIa) to (IIIc) was more than 95% as determined with $^1$H NMR analysis. The β-boration of (IIa) catalyzed with dtpf (10 mol %) was successfully performed also on the 15 mmol scale experiment.

Example 2c

Copper-Catalyzed (CuCO$_3$) Synthesis of Methyl-3-(4,4,5,5-tetramethyl-1,3,2-dioxaborolan-2-yl)-4-(2,4,5-trifluorophenyl)butanoate (IIIc) in Water in the Presence of Triphenylphosphine In a two-necked dry round bottom flask were placed CuCO$_3$ (0.04 mmol, 10.00 mg, 4 mol % according to starting material IIa) and Ph$_3$P (0.05 mmol, 12.60 mg, 5 mol %) under the nitrogen. Afterwards 2.5 mL of deionized water was added and the reaction mixture was vigorously (900 rpm) stirred at ambient temperature for 30 min. Than the boronating reagent bis(pinacolato)diboron (1.1 mmol, 280.0 mg, 1.10 equiv.) was added in one portion and such reaction mixture was stirred at ambient temperature for 30 min. Afterwards α,β-unsaturated ester (E)-methyl-4-(2,4,5-trifluorophenyl)-but-2-enoate (IIa) (1.0 mmol, 230.6 mg) was dropped into the reaction system and such reaction mixture was intensively stirred at ambient temperature for 24 hours. The reaction mixture was diluted with brine (5 mL) and extracted with EtOAc (2×30 mL). Combined organic layers were again washed with brine (30 mL), dried over Na$_2$SO$_4$ and organic solvent was removed under the reduced pressure. The crude product was simply purified with flash chromatography (SiO$_2$; EtOAc) to obtain 350 mg (97% yield) of liquid pure product (IIIc) as determined with $^1$H, $^{11}$B, $^{13}$C NMR and MS analysis.

Example 2d

Copper-Catalyzed ($CuCO_3$) Synthesis of Methyl-3-(4,4,5,5-tetramethyl-1,3,2-dioxaborolan-2-yl)-4-(2,4,5-trifluorophenyl)butanoate (IIIc) in Water in the Presence of 1,2-diphenylphosphinobenzene or 1,1'-bis(diphenylphosphino)ferrocene In a two-necked dry round bottom flask were placed $CuCO_3$ (0.04 mmol, 10.00 mg, 4 mol % according to starting material IIa) and 1,2-diphenylphosphinobenzene (dppbz; 0.05 mmol, 22.30 mg, 5 mol %) or 1,1'-bis(diphenylphosphino)ferrocene (dpff; 0.05 mmol, 27.72 mg) under the nitrogen. Afterwards 2.5 mL of deionized water was added and the reaction mixture was vigorously (900 rpm) stirred at ambient temperature for 30 min. Than the boronating reagent bis(pinacolato)diboron (1.1 mmol, 280.0 mg, 1.10 equiv.) was added in one portion and such reaction mixture was stirred at ambient temperature for 30 min. Afterwards α,β-unsaturated ester (E)-methyl-4-(2,4,5-trifluorophenyl)-but-2-enoate (IIa) (1.0 mmol, 230.6 mg) was dropped into the reaction system and such reaction mixture was intensively stirred at ambient temperature for 12 hours. The reaction mixture was diluted with brine (5 mL) and extracted with EtOAc (2×30 mL). Combined organic layers were again washed with brine (30 mL), dried over $Na_2SO_4$ and organic solvent was removed under the reduced pressure. The crude product was simply purified with flash chromatography ($SiO_2$; EtOAc) to obtain 310 mg (86%, yield) of liquid pure product (IIIc) as determined with $^1H$, $^{11}B$, $^{13}C$ NMR and MS analysis.

Example 2e

Copper-Catalyzed ($CuCO_3$) Synthesis of Methyl-3-(4,4,5,5-tetramethyl-1,3,2-dioxaborolan-2-yl)-4-(2,4,5-trifluorophenyl)butanoate (IIIc) in Water in the Presence of Bio-Based Ligand D-Glucosamine In a two-necked dry round bottom flask were placed D-glucosamine hydrochloride (0.05 mmol, 10.80 mg, 5 mol % according to starting material IIa), NaOH (0.06 mmol, 3.00 mg, 6 mol %) and were neutralized in water (2.5 mL). Afterwards dry $CuCO_3$ (0.04 mmol, 10.00 mg, 4 mol %) was added and the reaction mixture was vigorously (900 rpm) stirred at ambient temperature for 30 min. Than the boronating reagent bis(pinacolato)diboron (1.1 mmol, 280.0 mg, 1.10 equiv.) was added in one portion into the reaction system and stirred for 45 min. Finally, α,β-unsaturated ester (E)-methyl-4-(2,4,5-trifluorophenyl)-but-2-enoate (IIa) (1.0 mmol, 230.6 mg) was dropped into the reaction system and such reaction mixture was intensively stirred at ambient temperature for 18 hours. The reaction mixture was diluted with brine (5 mL) and extracted with EtOAc (2×30 mL). Combined organic layers were again washed with brine (30 mL), dried over $Na_2SO_4$ and organic solvent was removed under the reduced pressure. The crude product was simply purified with flash chromatography ($SiO_2$; EtOAc) to obtain 205 mg (57% yield) of liquid pure product (IIIc) as determined with $^1H$, $^{11}B$, $^{13}C$ NMR and MS analysis.

Example 2f

Copper-Catalyzed ($CuCO_3$) Asymmetric Synthesis of (R)-methyl-3-(4,4,5,5-tetramethyl-1,3,2-dioxaborolan-2-yl)-4-(2,4,5-trifluorophenyl)butanoate (IIIc) in Water in the Presence of Diphosphine Chiral Ligand BINAP In a two-necked dry round bottom flask were placed $CuCO_3$ (0.02 mmol, 5.00 mg, 4 mol % according to starting material IIa) and chiral ligand (R)-2,2'-bis(diphenylphosphino)-1,1'-binaphthalene (0.025 mmol, 5 mol %, 15.5 mg) under the nitrogen. Afterwards 2 mL of deionized water was added and the reaction mixture was vigorously (900 rpm) stirred at ambient temperature for 30 min. Than the boronating reagent bis(pinacolato)diboron (1.10 equiv., 0.55 mmol, 140.0 mg) was added in one portion into the reaction system and stirred for an hour. Finally, α,β-unsaturated ester (E)-methyl-4-(2,4,5-trifluorophenyl)-but-2-enoate (IIa) (0.5 mmol, 115.0 mg) was dropped into the reaction system and such reaction mixture was intensively stirred at ambient temperature for 20 hours. The reaction mixture was diluted with brine (5 mL) and extracted with EtOAc (2×30 mL). Combined organic layers were again washed with brine (30 mL), dried over $Na_2SO_4$ and organic solvent was removed under the reduced pressure. The crude product was simply purified with flash chromatography ($SiO_2$; EtOAc) to obtain 150 mg (84% yield) of liquid pure product (IIIc) as determined with $^1H$, $^{11}B$, $^{13}C$ NMR. HPLC chiral analysis of the obtained product (IIIc) showed an ee (70%).

Example 2q

Copper-Catalyzed ($CuCO_3$) Asymmetric Synthesis of Optical Active Methyl-3-(4,4,5,5-tetramethyl-1,3,2-dioxaborolan-2-yl)-4-(2,4,5-trifluorophenyl)butanoate (IIIc) in Water in the Presence of Ferrocenyl-Type Diphosphine Ligand Josiphos In a two-necked dry round bottom flask were placed $CuCO_3$ (0.02 mmol, 5.00 mg, 4 mol % according to starting material IIa) and chiral ligand 1,2-diphenylphosphino-ferrocenyl-ethyldi-tert-butylphosphine (0.025 mmol, 13.60 mg) under the nitrogen. Afterwards 2 mL of deionized water was added and the reaction mixture was vigorously (900 rpm) stirred at ambient temperature for 30 min. Than the boronating reagent bis(pinacolato)diboron (1.10 equiv., 0.55 mmol, 140.0 mg) was added in one portion into the reaction system and stirred for an hour. α,β-unsaturated ester (E)-methyl-4-(2,4,5-trifluorophenyl)-but-2-enoate (IIa) (0.5 mmol, 115.0 mg) was then dropped into the reaction system and such reaction mixture was intensively stirred at ambient temperature for 20 hours. The reaction mixture was diluted with brine (5 mL) and extracted with EtOAc (2×30 mL). Combined organic layers were again washed with brine (30 mL), dried over $Na_2SO_4$ and organic solvent was removed under the reduced pressure. The crude product was simply purified with flash chromatography ($SiO_2$; EtOAc) to obtain 155 mg (87% yield) of liquid pure product (IIIc) as determined with $^1H$, $^{11}B$, $^{13}C$ NMR. HPLC chiral analysis of (IIIc) showed an ee (86%).

Example 2h

Copper-Catalyzed ($CuCO_3$) Asymmetric Synthesis of Optical Active Methyl-3-(4,4,5,5-tetramethyl-1,3,2-dioxaborolan-2-yl)-4-(2,4,5-trifluorophenyl)butanoate (IIIc) in Water in the Presence of Ferrocenyl-Based Diphosphine Ligand Walphos In a two-necked dry round bottom flask were placed $CuCO_3$ (0.02 mmol, 5.00 mg, 4 mol % according to starting material IIa) and chiral ligand diphenylphosphino-phenyl-ferrocenyl-ethylbis[3,5-bis-trifluoromethyl)phenyl]phosphine (5 mol %, 0.025 mmol, 23.00 mg) under the nitrogen. Afterwards 2 mL of deionized water was added and the reaction mixture was vigorously (900 rpm) stirred at ambient temperature for 30 min. Than the boronating reagent bis(pinacolato)diboron (1.10 equiv., 0.55 mmol, 140 mg) was added in one portion into the reaction system and stirred for an hour. α,β-unsaturated ester (E)-methyl-4-(2,4,5-trifluorophenyl)-but-2-enoate (IIa) (0.5 mmol, 115.0 mg) was dropped into the reaction system and such reaction mixture was intensively stirred at ambient temperature for 20 hours. The reaction mixture was diluted with brine (5 mL) and extracted with EtOAc (2×30 mL). Combined organic layers were again washed with brine (30 mL), dried over $Na_2SO_4$ and organic solvent was removed under the reduced pressure. The crude product was simply purified with flash chromatography ($SiO_2$; EtOAc) to obtain 155 mg (84% yield) of liquid pure product (IIIc) as determined with $^1H$, $^{11}B$, $^{13}C$ NMR. HPLC chiral analysis of the (IIIc) showed an ee (95%).

Example 2i

Copper-Catalyzed ($CuCO_3$) Asymmetric Synthesis of Optical Active Methyl-3-(4,4,5,5-tetramethyl-1,3,2-dioxaborolan-2-yl)-4-(2,4,5-trifluorophenyl)butanoate (IIIc) in Water in the Presence of Chiral Diamine Ligand In a two-necked dry round bottom flask were placed $CuCO_3$ (0.04 mmol, 10.00 mg, 8 mol % according to starting material IIa) and chiral ligand N,N-dimethyl-1,2-diphenyl-1,2-ethylenediamine (0.05 mmol, 12.60 mg, 10 mol %) under the nitrogen. Afterwards 2 mL of deionized water was added and the reaction mixture was vigorously (900 rpm) stirred at ambient temperature for 30 min. Than the boronating reagent bis(pinacolato)diboron (1.10 equiv., 0.55 mmol, 140 mg) was added in one portion into the reaction system and stirred for an hour. α,β-unsaturated ester (E)-methyl-4-(2,4,5-trifluorophenyl)-but-2-enoate (IIa) (0.5 mmol, 115.0 mg) was dropped into the reaction system and such reaction mixture was intensively stirred at ambient temperature for 20 hours. The reaction mixture was diluted with brine (5 mL) and extracted with EtOAc (2×30 mL). Combined organic layers were again washed with brine (30 mL), dried over $Na_2SO_4$ and organic solvent was removed under the reduced pressure. The crude product was simply purified with flash chromatography ($SiO_2$; EtOAc) to obtain 150 mg (84% yield) of liquid pure product (IIIc) as determined with $^1H$, $^{11}B$, $^{13}C$ NMR. HPLC chiral analysis of the (IIIc) showed an ee (62%).

Example 2j

Copper-Catalyzed Asymmetric Synthesis of (R)-Methyl-3-(4,4,5,5-tetramethyl-1,3,2-dioxaborolan-2-yl)-4-(2,4,5-trifluorophenyl)butanoate (IIIc) in Organic Solvent in the Presence of Diphosphine Chiral Ligand BINAP In a two-necked dry round bottom flask equipped with an magnetic stir bar and rubber septums, were placed CuCl (10 mol %; 0.1 mmol, 10.2 mg), NaOt-Bu (13 mol %; 0.13 mmol, 12.5 mg) and chiral ligand (R)-2,2'-bis(diphenylphosphino)-1,1'-binaphthalene (10 mol % according to starting material IIa, 0.1 mmol, 62.0 mg) under the nitrogen atmosphere. Afterwards 1.5 mL of anhydrous THF was added and the reaction mixture was stirred at ambient temperature for 30 min. Than the borating agent bis(pinacolato)diboron (1.1 mmol, 280.0 mg, 1.10 equiv.) was added in three portions into the reaction mixture and after 30 min of intensive stirring α,β-unsaturated ester (E)-methyl-4-(2,4,5-trifluorophenyl)-but-2-enoate (IIa) (1.0 mmol, 230.60 mg) dissolved in 1 mL of THF was slowly added. Such reaction mixture was stirred at ambient temperature for 30 min and afterwards protic additive MeOH (1.5 mL; THF:MeOH=2:1) were added. Such reaction system was stirred for 16 hours at 30° C. The reaction mixture was concentrated under the reduced pressure, brine (5 mL) was added and mixture was transferred to a separating funnel. The aqueous layer was extracted with EtOAc (2×30 mL). Combined organic layers were washed with brine (30 mL), dried over $Na_2SO_4$ and organic solvent was removed under the reduced pressure. The crude product was simply purified with flash chromatography ($SiO_2$; $CH_2Cl_2$) to obtain 300 mg (84% yield) of liquid pure product (IIIc) as determined with $^1H$, $^{11}B$, $^{13}C$ NMR. HPLC chiral analysis of the (IIIc) showed an ee (86%).

Example 2k

Copper-Catalyzed Asymmetric Synthesis of Optical Active Methyl-3-(4,4,5,5-tetramethyl-1,3,2-dioxaborolan-2-yl)-4-(2,4,5-trifluorophenyl)butanoate (IIIc) in Organic Solvent in the Presence of Diphosphine Chiral Ligand Josiphos In a two-necked dry round bottom flask equipped with an magnetic stirrer and rubber septums, were placed CuCl (10 mol %; 0.1 mmol, 10.2 mg), NaOt-Bu (13 mol %; 0.13 mmol, 12.5 mg) and chiral ligand 1,2-diphenylphosphino-ferrocenyl-ethyldicyclohexyl-phosphine (10 mol % according to starting material IIa, 0.1 mmol, 64.0 mg) under the nitrogen atmosphere. Afterwards 1.5 mL of anhydrous THF was added and the reaction mixture was stirred at ambient temperature for 30 min. Than the borating agent bis(pinacolato)diboron (1.1 mmol, 280.0 mg, 1.10 equiv.) was added in three portions into the reaction mixture and after 30 min of intensive stirring α,β-unsaturated ester (E)-methyl-4-(2,4,5-trifluorophenyl)-but-2-enoate (IIa) (1.0 mmol, 230.60 mg) dissolved in 1 mL of THF was slowly added. Such reaction mixture was stirred at ambient temperature for 30 min and afterwards protic additive MeOH (1.5 mL; THF:MeOH=2:1) were added. The reaction system was stirred for 20 hours at 27° C. The reaction mixture was concentrated under the reduced pressure, brine (5 mL) was added and mixture was transferred to a separating funnel. The aqueous layer was extracted with EtOAc (2×30 mL). Combined organic layers were washed with brine (30 mL), dried over $Na_2SO_4$ and organic solvent was removed under the reduced pressure. The crude product was simply purified with flash chromatography ($SiO_2$; $CH_2Cl_2$) to obtain 255 mg (71.5% yield) of liquid pure product (IIIc) as determined with $^1H$, $^{11}B$ NMR. HPLC chiral analysis of the (IIIc) showed an ee (81%).

Example 2l

Copper-Catalyzed Synthesis of Methyl-3-(4,4,5,5-tetramethyl-1,3,2-dioxaborolan-2-yl)-4-(2,4,5-trifluorophenyl)butanoate (IIIc) in Water in the Absence of Ligand In a two-necked dry round bottom flask were placed $CuCO_3$ (0.075 mmol, 18.50 mg, 7.5 mol % according to starting material IIa) under the nitrogen. Afterwards 2.5 mL of deionized water was added followed by addition of boronating reagent bis(pinacolato)diboron (1.1 mmol, 280.0 mg, 1.10 equiv.) and such reaction mixture was vigorously (900 rpm) stirred at ambient temperature for 30 min. Afterwards α,β-unsaturated ester (E)-methyl-4-(2,4,5-trifluorophenyl)-but-2-enoate (IIa) (1.0 mmol, 230.6 mg) was dropped into the reaction system and obtained reaction mixture was intensively stirred at 60-70° C. for 20 hours. The reaction mixture was diluted with brine (5 mL) and extracted with EtOAc (2×30 mL). Combined organic layers were again washed with brine (30 mL), dried over $Na_2SO_4$ and organic solvent was removed under the reduced pressure. The crude product was purified with column chromatography ($SiO_2$; n-hexane: EtOAc=9:1) to obtain 108 mg of liquid pure product (IIIc) (30% yield) (IIIc) as determined with $^1H$, $^{11}B$, $^{13}C$ NMR and MS analysis.

Example 3a

The Synthesis of Methyl-3-hydroxy-4-(2,4,5-trifluorophenyl)butanoate (IVc) from (IIIc) Using Sodium Perborate Hydrate ($NaBO_3 \times H_2O$) as Oxidizing Agent The organoborane intermediate methyl-3-(4,4,5,5-tetramethyl-1,3,2-dioxaborolan-2-yl)-4-(2,4,5-trifluorophenyl)butanoate (IIIc) (4.6 mmol, 1.64 g) was dissolved in 12 mL of THF and stirred at ambient temperature under air atmosphere for a few minutes. Afterwards 12 mL of $H_2O$ was slowly added to the reaction system followed by sequential addition of oxidizing agent $NaBO_3 \times H_2O$ (18.4 mmol, 1.84 g, 4.0 equiv.) and such reaction mixture (suspension) was vigorously stirred at ambient temperature for 24 hours. The reaction mixture was diluted with water (10 mL), extracted with $CH_2Cl_2$ (2×50 mL), combined organic phases were washed with brine (30 mL), dried over anhydrous $Na_2SO_4$ and organic solvent was removed under reduced pressure. The obtained crude product was purified with flash chromatography ($SiO_2$; $CH_2Cl_2$) to obtain 975 mg (85% yield) of yellow liquid (IVc) determined with $^1H$ NMR, $^{13}C$ NMR and MS analysis.

$^1H$ NMR (500 MHz, $CDCl_3$, ppm) δ 7.13 (m, 1H), 6.90 (m, 1H), 4.24 (m, 1H), 3.71 (s, 3H), 3.14 (bs, OH), 2.80 (d, J=5 Hz, 2H), 2.43-2.56 (m, 2H).

$^{13}C$ NMR (125 MHz, $CDCl_3$, ppm) δ 34.9, 40.2, 51.9, 67.5, 105.3 (dd, J=28.8 Hz, J=21.3 Hz), 119.4 (dd, J=18.8 Hz, J=6.3 Hz), 121.1 (d, J=18.8 Hz), 145.6 (m), 147.6 (m), 156.0 (dd, J=243 Hz, J=7.0 Hz), 173.

Example 3b

The Synthesis of Methyl-3-hydroxy-4-(2,4,5-trifluorophenyl)butanoate (IVc) from (IIIc) Using Aqueous Hydrogen Peroxide ($H_2O_2$) as Oxidizing Agent In to a two-necked round bottom flask equipped with a magnetic stir bar, the solution of the organoborane intermediate methyl-3-(4,4,5,5-tetramethyl-1,3,2-dioxaborolan2-yl)-4-(2,4,5-trifluorophenyl)butanoate (IIIc) (1.0 mmol, 358 mg) in 3 mL THF was initiated through a rubber septum. Aqueous solution of sodium hydroxide (0.66 M; 1.0 mmol of NaOH in 1.50 mL of distilled water) was added and the reaction mixture was stirred for 30 min under ambient temperature. Afterwards 30% aqueous $H_2O_2$ (2.0 mmol, 206.1 μL, 2.0 equiv.) was slowly added and such reaction mixture was stirred for 24 hours at ambient temperature. The reaction mixture was concentrated under the reduced pressure and saturated with aqueous solution of $NaHCO_3$ (20 mL). The aqueous layer was extracted with $CH_2Cl_2$ (2×30 mL), combined organic layers were washed with brine (30 mL), dried over $Na_2SO_4$ and organic solvent was removed under the reduced pressure. The obtained crude yellow liquid product was purified with flash chromatography ($SiO_2$; EtOAc) to obtain 200 mg (80.6% yield) of yellow liquid (IVc) as determined with $^1H$ NMR and MS analysis.

Example 3c

The Synthesis of Methyl-3-hydroxy-4-(2,4,5-trifluorophenyl)butanoate (IVc) from (IIIc) Using Aqueous Solution of Sodium Hypochlorite (NaOCl) as Oxidizing Agent The organoborane intermediate methyl-3-(4,4,5,5-tetramethyl-1,3,2-dioxaborolan-2-yl)-4-(2,4,5-trifluorophenyl)butanoate (IIIc) (1 mmol, 358 mg) was dissolved in 2 mL of $CH_3OH$ and stirred at ambient temperature under air atmosphere for a few minutes. Afterwards the bleach (12-15% aqueous solution of NaOCl, 2.5 equiv. according to IIIc) was slowly dropping into the reaction system and vigorously stirred for 8 hours. The reaction mixture was first concentrated under the reduced pressure and organic residue was gently extracted with EtOAc (2×15 mL). The combined organic layers were than washed with saturated aqueous solution of $NaHCO_3$, dried over anhydrous $Mg_2SO_4$ and organic solvent was evaporated. The obtained crude product was purified with flash chromatography ($SiO_2$; EtOAc) to obtain 225 mg (90.7% yield) of (IVc) as determined with $^1H$ NMR spectroscopy.

Example 3d

The Synthesis of Methyl-3-hydroxy-4-(2,4,5-trifluorophenyl)butanoate (IVc) from (IIIc) Using Oxone as Oxidizing Agent The organoborane intermediate methyl-3-(4,4,5,5-tetramethyl-1,3,2-dioxaborolan-2-yl)-4-(2,4,5-trifluorophenyl)butanoate (IIIc) (0.5 mmol, 179 mg) was dissolved in 3 mL of THF and stirred at ambient temperature under air atmosphere for a few minutes. Afterwards aqueous solution of Oxone (3.0 equiv. according to IIIc) was slowly added to the reaction system and such reaction mixture (suspension) was vigorously stirred at ambient temperature for 24 hours. The THF was first evaporated under reduced pressure and residue was extracted with EtOAc (2×20 mL). The combined organic layers were than washed with saturated aqueous solution of $NaHCO_3$, dried over anhydrous $Mg_2SO_4$ and organic solvent was evaporated. The obtained crude product was purified with flash chromatography ($SiO_2$; EtOAc) to obtain 103 mg (83.8% yield) of (IVc) as determined with $^1H$ NMR spectroscopy.

Example 3e

One-pot β-boration/oxidation Synthetic Protocol to Secondary Alcohol Methyl-3-hydroxy-4-(2,4,5-trifluorophenyl)butanoate (IVc) from Intermediate (IIa)

After the completion of the β-boration of the intermediate (IIa) (Example 2a-b) the reaction mixture was diluted with THF (5 mL) and $H_2O$ (7.5 mL). Afterwards sodium perborate hydrate (4.0 mmol, 399.2 mg, 4.0 equiv.) were sequentially added into the reaction mixture and the reaction system was vigorously stirred at ambient temperature for 24 hours under air. The reaction mixture was concentrated under the reduced pressure, than extracted with EtOAc (3×20 mL) and combined organic layers were gently washed with brine (30 mL) and dried over anhydrous $Na_2SO_4$. After the removal of the organic solvent under reduced pressure, a crude dark yellow liquid was obtained which was further purified with flash chromatography (SiO$_2$; EtOAc) to obtain 220 mg (88% yield) of a crude yellow viscous liquid (IVc). The structure of (VIc) was confirmed by $^1$H and $^{13}$C NMR analysis and successfully determined by MS analysis.

Example 4a

Direct Synthesis of Methyl-3-amino-4-(2,4,5-trifluorophenyl)butanoate (Ia) from Organoborane (IIIc) Using Freshly Prepared Chloramine To a solution of methyl-3-(4,4,5,5-tetramethyl-1,3,2-dioxaborolan-2-yl)-4-(2,4,5-trifluorophenyl)butanoate (IIIc) (1.0 mmol; 358 mg) in anhydrous THF (5 mL) under nitrogen, was slowly added CH$_3$MgCl (3 M in THF, 2.0 mmol, 666 µL, 2.0 equiv.) and the solution was stirred for 1 hour at 0° C. Afterwards aqueous ammonium hydroxide (25% aqueous solution, 3.0 mmol, 224 µL, 3.0 equiv.) and 3 mL of dry THF were added following by slow addition of sodium hypochlorite (15% aqueous solution, 3.2 mmol, 1.32 mL) for the in situ generation of the chloramine (NH$_2$Cl). The reaction mixture was stirred for 30 min at 0° C., then slowly heated to room temperature and vigorously stirred for 20 hours. Aqueous HCl (1 M, 5 mL) was added, the mixture was extracted with MTBE (30 mL) and organic phase was separated from the aqueous in separating funnel (organic phase 1). Afterwards aqueous NaOH (5 M, 5 mL) was added to the acidic aqueous layer and gently extracted with MTBE (3×30 mL). The combined organic layers (organic phase 2) were dried over Na$_2$SO$_4$ and solvent was evaporated under reduced pressure. The obtained crude reaction mixture (135 mg, 54% yield) was analyzed with HPLC and the compound (Ia) was confirmed with HPLC-MS analysis.

Example 4b

Direct Synthesis of Methyl-3-amino-4-(2,4,5-trifluorophenyl)butanoate (Ia) From Organoborane (IIIc) Using Hydroxylamine-O-Sulfonic Acid (HSA)

To a solution of methyl-3-(4,4,5,5-tetramethyl-1,3,2-dioxaborolan-2-yl)-4-(2,4,5-trifluorophenyl)butanoate (IIIc) (1.0 mmol; 358 mg) in anhydrous THF (5 mL) was slowly added CH$_3$MgCl (3 M in THF, 2.0 mmol, 666 µL, 2.0 equiv.) and the solution was stirred under nitrogen for 1 hour at 0° C. Afterwards predried HSA (2.2 mmol, 226 mg) was slowly added into solution using a solid addition tube and formed yellow suspension was stirred then at ambient temperature for 24 hours. Aqueous HCl (1 M, 5 mL) was added, the mixture was extracted with MTBE (30 mL) and organic phase was separated from the aqueous in separating funnel (organic phase 1). Afterwards aqueous NaOH (5 M, 5 mL) was added to the acidic aqueous layer and gently extracted with MTBE (3×30 mL). The combined organic layers (organic phase 2) were dried over Na$_2$SO$_4$ and solvent was evaporated under reduced pressure. The obtained crude reaction mixture (110 mg, 45% yield) was analyzed with $^1$H NMR and compound (Ia) was determined/confirmed with HPLC-MS analysis.

Example 4c

Direct Synthesis of Methyl-3-(benzylamino)-4-(2,4,5-trifluorophenyl)butanoate (Ib) from Organoborane (IIIc)

To a solution of methyl-3-(4,4,5,5-tetramethyl-1,3,2-dioxaborolan-2-yl)-4-(2,4,5-trifluorophenyl)butanoate (IIIc) (0.5 mmol; 180.0 mg) in toluene (2.5 mL) was slowly added BCl$_3$ (1 M solution in toluene, 2.5 mmol, 2.5 mL, 5.0 equiv. according to IIIc) and such a reaction mixture was stirred under nitrogen for several hours at room temperature. Afterwards reaction system was cooled down on an ice bath and benzylazide (1.5 mmol, 0.2 mL) was slowly dropped into the system. Slow effervescence as a loss of nitrogen was observed. Such a reaction mixture was vigorously stirred at room temperature overnight. The reaction mixture was quenched by 2 M aqueous solution of NaOH and extracted with 3 portions of MTBE (25 mL). Combined organic layers were finally washed with brine (50 mL), dried over Na$_2$SO$_4$ and organic solvent was removed under the reduced pressure. The obtained crude product was purified with column chromatography (SiO$_2$, hexane:ethyacetate=2:1) and yellowish liquid pure product (Ib) (80 mg, 47% yield) was obtained and confirmed with $^1$H and $^{13}$C NMR analysis.

$^1$H NMR (500 MHz, CDCl$_3$, ppm) δ 7.28 (m, 5H), 7.04 (m, 1H), 6.90 (m, 1H), 3.84 (dd, J=6.5 Hz, J=2.2 Hz, 2H), 3.67 (s, 3H), 3.25 (pentet, J=6.3 Hz, 1H), 2.90 (dd, J=14.0 Hz, J=6.3 Hz, 1H), 2.72 (dd, J=14 Hz, J=6.3 Hz, 1H), 2.45 (dd, J=21.0 Hz, J=6.3 Hz, 2H), 1.95 (bs, NH).

$^{13}$C NMR (125 MHz, CDCl$_3$, ppm) δ 172.3, 156.1 (dd, J=235.0 Hz, J=1.25 Hz), 148.5 (dd, J=247.0 Hz, J=1.25 Hz), 146.5 (dd, J=267 Hz, J=15 Hz), 140.0, 128.4, 128.0, 127.0, 122.1, 119.1 (dd, J=18.75 Hz, J=5.0 Hz), 105.3 (dd, J=28.75 Hz, J=21.25 Hz), 54.4, 51.6, 51.0, 38.4, 33.0.

Example 5a

Synthesis of Methyl 3-acetamido-4-(2,4,5-trifluorophenyl)butanoate from Methyl 3-hydroxy-4-(2,4,5-trifluorophenyl)butanoate (IVc)

In a thick-walled glass vial equipped with an magnetic stir bar was placed methyl 3-hydroxy-4-(2,4,5-trifluorophenyl)butanoate (IVc) (2.0 mmol 115 mg) and then acetonitrile (3 mL) was added to obtain clear solution. Afterwards trifluoromethanesulfonic acid (15.0 mmol, 1.32 mL) was slowly added through the septum followed by addition of water (15.0 mmol, 0.3 mL) and reaction mixture was slowly heated to 80° C. Such reaction system was stirred for 16 hours at 80° C. Solvent was first evaporated under reduced pressure, organic residue was neutralized with saturated aqueous solution of NaHCO$_3$ (4 mL) and gently extracted with EtOAc (2×30 mL). The combined organic phases were dried over MgSO$_4$ and the solvent was evaporated under reduced pressure. The crude product was purified with column chromatography (SiO$_2$, n-hexane:ethylacetate=1:1) to obtain oily product (368 mg; 63.6% yield) which was analyzed and determined with $^1$H, $^{13}$C NMR and MS analysis.

$^1$H NMR (500 MHz, CDCl$_3$, ppm) δ 7.05 (m, 1H), 6.90 (m, 1H), 5.41 (pentet, 1H), 3.70 (s, 3H), 3.01 (dd, J=15 Hz, J=5 Hz, 1H), 2.90 (dd, J=15 Hz, J=5 Hz, 1H), 2.60 (m, 2H), 2.01 (s, 3H).

$^{13}$C NMR (125 MHz, CDCl$_3$, ppm) δ 20.9, 32.4, 38.0, 51.9, 69.5, 105.5 (dd, J=28.8 Hz, J=21.3 Hz), 119.3 (dd, J=18.8 Hz, J=6 Hz), 120.3 (d, J=18.8 Hz), 146.3 (m), 148.1 (m), 156.0 (m), 169.9 (CO), 170.3 (CO).

MS (CI) m/z (%) 291 (M+1, 25%), 259 (70%), 231 (100%), 199 (76%).

Example 5b

Synthesis of Methyl-3-(benzylamino)-4-(2,4,5-trifluorophenyl)butanoate (Ib) from Methyl 3-hydroxy-4-(2,4,5-trifluorophenyl)butanoate (IVc) Catalyzed by Iridium Catalysts In a two-necked dry round bottom flask equipped with an magnetic stirrer and rubber septums, were placed catalyst

[CpIrCl$_2$]$_2$ (5 mol % according to IVc) and NaHCO$_3$ (5 mol %) under the nitrogen atmosphere. Afterwards 5 mL of toluene was added, the reaction mixture was stirred at ambient temperature for 15 min followed by addition of methyl-3-hydroxy-4-(2,4,5-trifluorophenyl)butanoate (IVc) (1.0 mmol, 248.0 mg). After an hour of stirring and heating the reaction mixture at 120° C., benzylamine (1.0 mmol, 107.0 mg) was slowly dropped into the reaction system and such reaction mixture was left at 120 to 130° C. overnight. The reaction mixture was concentrated under reduced pressure, extracted with EtOAc, organic phases were washed with brine and dried over Na$_2$SO$_4$. After evaporation of the solvent under reduced pressure the obtained crude product was purified with flash chromatography (SiO$_2$; CH$_2$Cl$_2$) to obtain 75 mg (22% yield). The compound (Ib) was determined/confirmed with HPLC-MS analysis and $^1$H NMR.

Example 5c

Synthesis of Methyl-3-(benzylamino)-4-(2,4,5-trifluorophenyl)butanoate (Ib) from Methyl 3-hydroxy-4-(2,4,5-trifluorophenyl)butanoate (IVc) Catalyzed by Ruthenium Catalysts In a double-wall glass tube equipped with an magnetic stirrer and rubber septum, were placed catalyst Ru$_3$(CO)$_{12}$ (5 mol % according to IVc) and 2-[dicyclohexyl]phosphine)-1-phenyl-1H-pyrole (10 mol %) under the nitrogen atmosphere. Afterwards 1 mL of toluene was added, the reaction mixture was stirred at ambient temperature for 15 min followed by addition of methyl-3-hydroxy-4-(2,4,5-trifluorophenyl)butanoate (IVc) (0.2 mmol, 50.0 mg) dissolved in 0.5 mL of toluene. After an hour of stirring and heating the reaction mixture at 120° C., benzylamine (1.5 equiv.) was slowly dropped into the reaction system and such reaction mixture was left at 120 to 130° C. overnight. The reaction mixture was concentrated under reduced pressure, extracted with EtOAc, organic phases were washed with brine and dried over Na$_2$SO$_4$. After evaporation of the solvent under reduced pressure the obtained crude product was purified with flash chromatography (SiO$_2$; CH$_2$Cl$_2$) to obtain 20 mg (30% yield) of pure compound (Ib). The (Ib) was determined/confirmed with HPLC-MS analysis and $^1$H NMR.

Example 5d

Synthesis of Methyl-3-(benzylamino)-4-(2,4,5-trifluorophenyl)butanoate (Ib) from Methyl 3-hydroxy-4-(2,4,5-trifluorophenyl)butanoate (IVc) Catalyzed by Iridium Catalyst in Pure Aqueous Medium In a double-wall test tube equipped with an magnetic stirrer and septum, were placed catalyst [CpIrI$_2$]$_2$ (5 mol % according to IVc) and starting material methyl 3-hydroxy-4-(2,4,5-trifluorophenyl)butanoate (IVc) (0.7 mmol, 174.0 mg) under the nitrogen atmosphere. Afterwards 2.5 mL of deionized water was added and such heterogenic mixture was intensively stirred (900 rpm) at 115° C. for 15 to 30 min. Benzylamine (0.5 mmol, 60.0 µL) was then slowly dropped into the reaction system and such reaction mixture was vigorously stirred at 115° C. overnight. The reaction mixture was quenched with brine, extracted with EtOAc and organic phases were dried over Na$_2$SO$_4$. After evaporation of the solvent under reduced pressure the crude product was purified with column chromatography (SiO$_2$, hexane:ethyacetate=2: 1) and liquid pure product (Ib) (80 mg, 34% yield) was obtained and determined with $^1$H, $^{13}$C NMR analysis.

Example 5e

Synthesis of Methyl-3-(benzylamino)-4-(2,4,5-trifluorophenyl)butanoate (Ib) from Methyl 3-hydroxy-4-(2,4,5-trifluorophenyl)butanoate (IVc) Catalyzed by Iron Catalysts In a double-wall glass tube equipped with an magnetic stirrer and septum, were placed anhydrous FeCl$_3$ (5 mol % according to IVc, 0.025 mmol), L-pyroglutamic acid (10 mol %, 0.05 mmol) and 1,2,3,4,5-pentamethylcyclopenta-1,3-diene (10 mol %, 0.05 mmol) under the nitrogen atmosphere. Afterwards 0.5 mL of α,α,α-trifluorotoluene was added and the reaction mixture was heated at 100° C. where methyl 3-hydroxy-4-(2,4,5-trifluorophenyl)butanoate (IVc) (0.5 mmol, 124.0 mg) was dropped and such reaction system was stirred for 30 min. Afterwards benzylamine (1.25 mmol, 136.5 µL) was slowly dropped into the reaction system and such reaction mixture was heated to 160° C. and left there for 12 hours. The reaction mixture was quenched with an aqueous solution of ammonium chloride, concentrated under reduced pressure, extracted with EtOAc, organic phases were washed with brine and dried over Na$_2$SO$_4$. After evaporation of the solvent under reduced pressure the crude product was purified with flash chromatography (SiO$_2$; CH$_2$Cl$_2$) to obtain 50 mg (29% yield) of a pure (Ib). The compound (Ib) was determined/confirmed with HPLC-MS analysis and $^1$H NMR.

LIST OF REFERENCES

WO 03/004498
WO 09/06447
WO 04/085378
WO 05/097733
WO 06/081151
WO 04/085661
WO 04/087650
US 2009/0192326
US 2006/0052382
WO 09/045,507
WO 2010/122578
Hansen, K. B.; et. al. *J. Am. Chem. Soc.* 2009, 131, 8798-8804.
Hansen K. B.; et. al. *Org. Process Res. Dev.* 2005, 9, 634-639.
Hsiao, Y.; et. al. *J. Am. Chem. Soc.*, 2004, 126, 9918-9919.
Kubryl, M.; et. al. *Tetrahedron Asymmetry* 2006, 17, 205-209.
Liu, F.; et. al. *J. Chem. Res.* 2010, 34, 230-232.
Savile, C. K.; et. al. *Science* 2010, 329, 305-309.
Desai, A.; et. al. *Angew. Chem. Int. Ed.* 2011, 50, 2-5.

The following pages of the description refer to the embodiments of the invention listed as separate items:

1. A process for the preparation of an intermediate of formula I

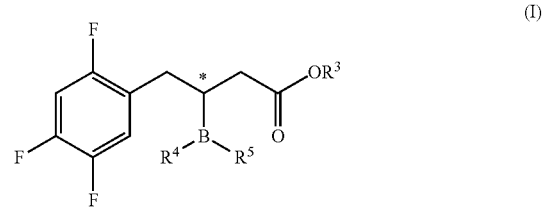

wherein the stereogenic center marked with an * is either in (R)- or (S)-configuration at marked center, or it is in racemic form, and wherein $R^4$ and $R^5$ are identical or different, and are independently selected from
(i) hydrogen;
(ii) alkyl residues optionally chiral, having from 1 to 12 carbon atoms, wherein the alkyl residues are optionally aryl and/or aryloxy substituted;
(iii) alkyloxy residues optionally chiral, having from 1 to 12 carbon atoms, wherein the alkyloxy residues are optionally aryl substituted;
(iv) aryl residues optionally chiral, having from 6 to 24 carbon atoms, wherein the aryl residues are optionally alkyl and/or alkyloxy substituted;
(v) aryloxy residues optionally chiral, having from 6 to 24 carbon atoms, wherein the aryloxy residues are optionally alkyl substituted;
(vi) benzyl;
(vii) alkaloyl residues optionally chiral, having from 2 to 13 carbon atoms, wherein the alkaloyl residues are optionally aryl substituted;
(viii) aroyl residues optionally chiral, having from 7 to 25 carbon atoms, wherein the aryloxy residues are optionally alkyl substituted; and
(ix) alkoxycarbonyl residues optionally chiral, having from 2 to 13 carbon atoms;
(x) aryloxycarbonyl residues optionally chiral, having from 7 to 25 carbon atoms; and
(xi) tosyl;
wherein $R^3$ is selected from alkyl residues having from 1 to 6 carbon atoms;
the process comprising the steps of:
(a) providing an intermediate of formula II

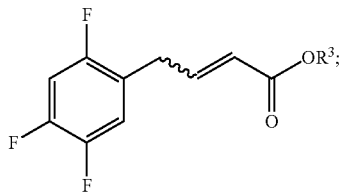

(II)

(b) reacting the intermediate of formula II with a borating agent in a suitable solvent to obtain an intermediate of formula III,

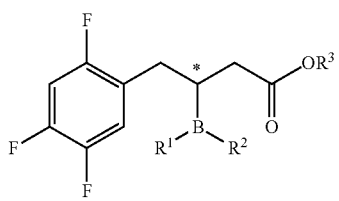

(III)

wherein the stereogenic center marked with an * is either in (R)- or (S)-configuration at marked center, or it is in racemic form, and wherein $R^1$ and $R^2$ are identical or different, and are selected from
(i) alkyl or alkoxy residues, each having from 1 to 12 carbon atoms, wherein each alkyl or alkoxy residue is optionally aryl substituted,
(ii) aryl or aryloxy residues, each having from 6 to 14 carbon atoms, wherein each aryl or aryloxy residue is optionally alkyl substituted;
(iii) halides; and
(iv) wherein $R^1$ and $R^2$ optionally form a chiral or non-chiral 5 to 10, particularly 5 to 6, membered mono or bicyclic ring, wherein the ring is optionally substituted at least one position with an alkyl residue having from 1 to 12 carbon atoms and/or an aryl residue having from 6 to 14 carbon atoms, and wherein $R^1$ and $R^2$ optionally form an O-benzenedioxy residue;
(c) converting the intermediate of formula III to the intermediate of formula I.

2. The process of item 1, wherein $R^4$ and $R^5$ are identical, and are selected from
(i) hydrogen;
(ii) alkyl residues optionally chiral, having from 1 to 12 carbon atoms, wherein the alkyl residues are optionally aryl and/or aryloxy substituted;
(iii) alkyloxy residues optionally chiral, having from 1 to 12 carbon atoms, wherein the alkyloxy residues are optionally aryl substituted;
(iv) aryl residues optionally chiral, having from 6 to 24 carbon atoms, wherein the aryl residues are optionally alkyl and/or alkyloxy substituted;
(v) aryloxy residues optionally chiral, having from 6 to 24 carbon atoms, wherein the aryloxy residues are optionally alkyl substituted;
(vi) benzyl;
(vii) alkaloyl residues optionally chiral, having from 2 to 13 carbon atoms, wherein the alkaloyl residues are optionally aryl substituted;
(viii) aroyl residues optionally chiral, having from 7 to 25 carbon atoms, wherein the aryloxy residues are optionally alkyl substituted; and
(ix) alkoxycarbonyl residues optionally chiral, having from 2 to 13 carbon atoms;
(x) aryloxycarbonyl residues optionally chiral, having from 7 to 25 carbon atoms; and
(xi) tosyl;
and are particularly hydrogen or N-α-methylbenzyl or methyl.

3. The process of item 1, wherein $R^4$ and $R^5$ are different, and are independently selected from
(i) hydrogen;
(ii) alkyl residues optionally chiral, having from 1 to 12 carbon atoms, wherein the alkyl residues are optionally aryl and/or aryloxy substituted;
(iii) alkyloxy residues optionally chiral, having from 1 to 12 carbon atoms, wherein the alkyloxy residues are optionally aryl substituted;
(iv) aryl residues optionally chiral, having from 6 to 24 carbon atoms, wherein the aryl residues are optionally alkyl and/or alkyloxy substituted;
(v) aryloxy residues optionally chiral, having from 6 to 24 carbon atoms, wherein the aryloxy residues are optionally alkyl substituted;
(vi) benzyl;
(vii) alkaloyl residues optionally chiral, having from 2 to 13 carbon atoms, wherein the alkaloyl residues are optionally aryl substituted;
(viii) aroyl residues optionally chiral, having from 7 to 25 carbon atoms, wherein the aryloxy residues are optionally alkyl substituted; and
(ix) alkoxycarbonyl residues optionally chiral, having from 2 to 13 carbon atoms;

(x) aryloxycarbonyl residues optionally chiral, having from 7 to 25 carbon atoms; and (xi) tosyl;

and particularly $R^4$ is hydrogen and $R^5$ is tosyl, or $R^4$ is hydrogen and $R^5$ is tosyl, or, $R^4$ is hydrogen and $R^5$ is benzyl', or $R^4$ is hydrogen and $R^5$ is O-benzyl, or $R^4$ is hydrogen and $R^5$ is O-methyl, or $R^4$ is benzyl and $R^5$ is N-α-methylbenzyl, or $R^4$ is hydrogen and $R^5$ is tert-butyl-oxy-carbonyl, or $R^4$ is hydrogen and $R^5$ is benzyl-oxy-carbonyl, or $R^4$ is hydrogen and $R^5$ is benzoyl, or $R^4$ is hydrogen and $R^5$ is acetyl, or $R^4$ is hydrogen and $R^5$ is N-α-methylbenzyl, or $R^4$ is hydrogen and $R^5$ is phenyl-O-methyl.

4. The process of any of the preceding items, wherein the chiral aryl residues are selected from N-α-methylbenzyl, N-bis[α-methylbenzyl], 2-methoxybenzyl-1-phenylethyl, 3,4-dimethoxybenzyl-1-phenylethyl, and N-benzyl-1-phenylethyl.

5. The process of any of the preceding items, wherein the halides are selected from chloride, bromide and iodide, and are particularly chloride.

6. The process of any of the preceding items, wherein $R^3$ is selected from methyl, ethyl, propyl, cyclopropyl, butyl, pentyl, hexyl, isopropyl, isopentyl, tert-butyl and is particularly methyl.

7. The process of item 1, wherein the intermediate of formula I is (Ia)

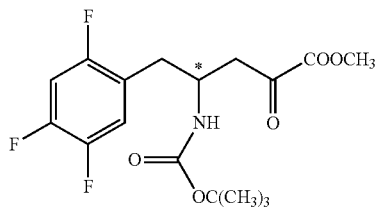

(Ib)

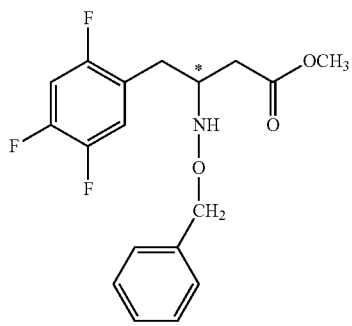

(Ic)

(Id)

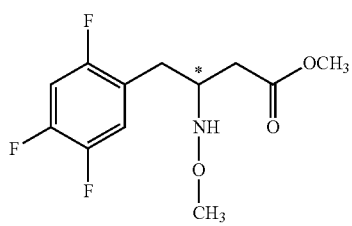

(Ie)

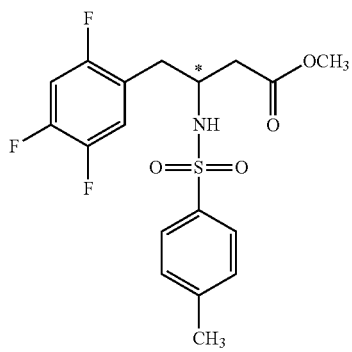

(If)

(Ig)

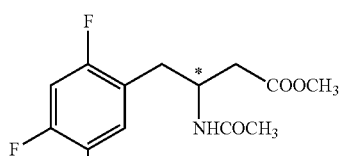

(Ih)

(Ii)

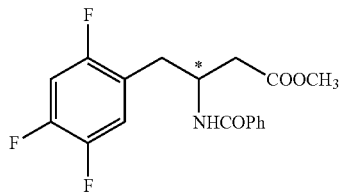

-continued

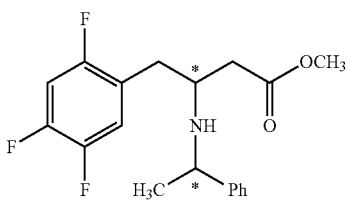
(Ij)

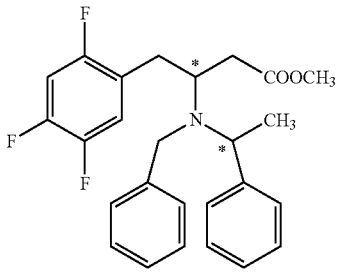
(Ik)

wherein the stereogenic center marked with an * is either in (R)- or (S)-configuration at marked center, or it is in racemic form.

8. The process of any of the preceding items, wherein the intermediate of formula II in step (a) is provided by a process as defined in any of items 103 to 120.

9. The process of any of the preceding items, wherein in step (b) the borating agent is selected from optionally chiral boronic esters, optionally chiral alkyl boranes, and optionally alkyl-aryl boranes.

10. The process of item 9, wherein the boronic ester is selected from bis(pinacolato)diboron, bis(catecholato)diboron, bis(neopentyl-glycolato)diboron, bis(hexylene-glycolato)diboron, pinacolborane, and catecholborane.

11. The process of item 9, wherein the alkyl borane is selected from (S)-bis(pinene)borane, (R)-bis(pinene)borane and bis(terpenoyl)borane.

12. The process of item 9, wherein the alkyl-aryl borane is selected from 2-methyl-5-phenylborolane and 2,5-diphenylborolane.

13. The process of any of the preceding items, wherein in step (b) the borating agent is present in an amount of 1.05-1.5 equivalents, particularly of 1.1-1.3 equivalents, with respect to the intermediate of formula II.

14. The process of any of the preceding items, wherein step (b) is a transition metal catalyzed process, particularly a transition metal catalyzed process using a catalyst comprising a transition metal compound.

15. The process of any of the preceding items, wherein step (b) is a transition metal catalyzed process, particularly a transition metal catalyzed process using a catalyst comprising a transition metal compound and at least one ligand.

16. The process of item 14 or 15, wherein in step (b) the transition metal compound is selected from copper(I) chloride, copper(II) bromide, copper(II) carbonate, copper(I) iodide, copper(I) oxide, copper(II) oxide, copper(I) acetate, copper(II) triflate, and any combination thereof.

17. The process of item 16, wherein in step (b) the transition metal compound is copper(II) carbonate.

18. The process of items 14 to 16, wherein in step (b) the transition metal compound is present in an amount of 1-15 mol %, particularly of 2-12 mol %, and more particularly 4-10 mol % to the intermediate of formula II.

19. The process of any of the preceding items, wherein in step (b) the suitable solvent is selected from tetrahydrofuran (THF), dimethylformamide (DMF), toluene, MeOH, water, 2-methyltetrahydrofuran, and any combination thereof.

20. The process of item 19, wherein in step (b) the suitable solvent is water.

21. The process of any of the preceding items, wherein in step (b) the transition metal compound is copper(II) carbonate and the suitable solvent is water.

22. The process of item 15, wherein in step (b) the at least one ligand is selected from monophosphine ligands, diphosphine ligands, and N,O-containing ligand, and any combination thereof.

23. The process of item 15 or 22, wherein in step (b) the at least one ligand is selected from monophosphine ligands, and is particularly triphenylphosphine, trimethylphosphine, tricyclohexylphosphine, tributylphosphine, tri-(o-tolyl)-phosphine, tri-(2-furyl)phosphine, tris(dimethylamino)-phosphine, tribenzylphosphine, tripyrolydinophosphine, tris(4-methoxyphenyl)phosphine and any combination thereof.

24. The process item 15 or 22, wherein in step (b) the at least one ligand is selected from diphosphine ligands, and is particularly 1,2-bis(diphenyl-phosphino)benzene, 1,1,-bis(di-tert-butylphosphino)ferrocene, (oxydi-2,1-phenylene) bis-(diphenylphosphine), and any combination thereof.

25. The process of item 15 or 22, wherein in step (b) the ligand is selected from N,O-containing ligand, in particular D-glucozamine.

26. The process of any of items 15 to 25, wherein in step (b) the ligand is chiral selected from (R)-2,2'-bis(diphenylphosphino)-1,1-binaphthalene, (S)-2,2'-bis(diphenylphosphino)-1,1-binaphthalene, (S,R)-(diphenylphosphino)-ferrocenyl-ethyldi-tert-butylphosphine, (R,S)-(diphenylphosphino)-ferrocenyl-ethyldi-tert-butylphosphine,(S)-1-($S_p$)-2-[2-(diphenylphosphino)-phenyl]-ferrocenyl-ethylbis[3,5-bis(trifluoromethyl) phenyl]phosphine, (R)-1-($R_p$)-2-[2-(diphenylphosphino)-phenyl]-ferrocenyl-ethylbis[3,5-bis(trifluoromethyl) phenyl]phosphine, (S)-4-tert-butyl-2-[($S_p$)-2-(diphenylphosphino)ferrocenyl]-2-oxazoline, (R)-4-tert-butyl-2-[($S_p$)-2-(diphenylphosphino)ferrocenyl]-2-oxazoline, (1S,1'S)-1,1'-bis[bis[3,5-bis(trifluoromethyl) phenyl]phosphino]-2,2'-bis[(S)-dimethylamino) phenylmethyl], (1R,1'R)-1,1'-bis[bis[3,5-bis (trifluoromethyl)phenyl]phosphino]-2,2'-bis[(R)-(dimethylamino)phenylmethyl], and any combination thereof, and is particularly (R)-2,2'-bis(diphenylphosphino)-1,1-binaphthalene, (S)-2,2'-bis(diphenylphosphino)-1,1-binaphthalene, and (S)-1-($S_p$)-2-[2-(diphenylphosphino)-phenyl]-ferrocenyl-ethylbis[3,5-bis (trifluoromethyl)phenyl]phosphine, (R)-1-($R_p$)-2-[2-(diphenylphosphino)-phenyl]-ferrocenyl-ethylbis[3,5-bis (trifluoromethyl)phenyl]phosphine.

27. The process of any of items 15 to 26, wherein in step (b) the at least one ligand is present in an amount of 1-15 mol %, particularly of 2-12 mol %, and more particularly 4-10 mol %, with respect to the intermediate of formula II.

28. The process of any of items 15 to 27, wherein in step (b) the transition metal compound is copper(II) carbonate and the suitable solvent is water and wherein at least one ligand is chiral.

29. The process of any of items 15 to 18 and 22 to 27, wherein the transition metal catalyzed process is carried out in the presence of a base, particularly wherein the base is selected from NaOt-Bu, KOt-Bu, $K_2CO_3$, $Na_2CO_3$, $MgCO_3$, $Na_3PO_4$, $K_3PO_4$, KOAc, NaOAc, and any combination thereof, more particularly NaOt-Bu.

30. The process of item 29, wherein the base is present in an amount of 2-25 mol %, particularly of 4-20 mol %, and more particularly 6-15 mol %, with respect to the intermediate of formula II.

31. The process of any of the preceding items, wherein in step (b) the reaction is carried out at a temperature of 15° C. to 30° C., particularly from 20° C. to 25° C., and more particularly room temperature.

32. The process of any of items 1 to 13, wherein step (b) is a transition metal free catalyzed process, particularly a transition metal free catalyzed process using a base and at least one ligand.

33. The process of item 32, wherein in step (b) the base is selected from cesium carbonate, cesium hydroxide, cesium phosphate, cesium chloride, cesium fluoride, cesium iodide, and any combination thereof, and is preferably cesium carbonate.

34. The process of item 30 or 33, wherein in step (b) the base is present in an amount of 5-40 mol %, particularly of 8-30 mol %, and more particularly 10-20 mol % to the intermediate of formula II.

35. The process of any of items 30 to 34, wherein in step (b) the at least one ligand is selected from monophosphine ligands, diphosphine ligands, and any combination thereof.

36. The process of any of items 30 to 35, wherein in step (b) the at least one ligand is selected from monophosphine ligands, and is particularly triphenylphosphine, trimethylphosphine, tricyclohexylphosphine, tributylphosphine, tri-(o-tolyl)-phosphine, tri-(2-furyl)phosphine, tris(dimethylamino)-phosphine, tribenzylphosphine, tripyrolydinophosphine, tris(4-methoxyphenyl)phosphine and any combination thereof.

37. The process of any of items 30 to 35, wherein in step (b) the at least one ligand is selected from diphosphine ligands, and is particularly 1,2-bis(diphenyl-phosphino)benzene, 1,1,-bis(di-tert-butylphosphino)ferrocene, (oxydi-2,1-phenylene)bis-(diphenylphosphine), and any combination thereof.

38. The process of any of items 30 to 35, wherein the ligand is chiral and selected from (R)-2,2'-bis(diphenylphosphino)-1,1-binaphthalene, (S)-2,2'-bis(diphenylphosphino)-1,1-binaphthalene, (S,R)-(diphenylphosphino)-ferrocenyl-ethyldi-tert-butylphosphine, (R,S)-(diphenylphosphino)-ferrocenyl-ethyldi-tert-butylphosphine,(S)-1-($S_p$)-2-[2-(diphenylphosphino)-phenyl]-ferrocenyl-ethylbis[3,5-bis(trifluoromethyl) phenyl]phosphine, (R)-1-($R_p$)-2-[2-(diphenylphosphino)-phenyl]-ferrocenyl-ethylbis[3,5-bis(trifluoromethyl) phenyl]phosphine, (S)-4-tert-butyl-2-[($S_p$)-2-(diphenylphosphino)ferrocenyl]-2-oxazoline, (R)-4-tert-butyl-2-[($S_p$)-2-(diphenylphosphino)ferrocenyl]-2-oxazoline, (1S,1'S)-1,1'-bis[bis[3,5-bis(trifluoromethyl) phenyl]phosphino]-2,2'-bis[(S)-dimethylamino) phenylmethyl], (1R,1'R)-1,1'-nis[bis[3,5-bis (trifluoromethyl)phenyl]phosphino]-2,2'-bis[(R)-(dimethylamino)phenylmethyl], and any combination thereof, and is particularly (R)-2,2'-bis(diphenylphosphino)-1,1-binaphthalene, (S)-2,2'-bis(diphenylphosphino)-1,1-binaphthalene, and (S)-1-($S_p$)-2-[2-(diphenylphosphino)-phenyl]-ferrocenyl-ethylbis[3,5-bis (trifluoromethyl)phenyl]phosphine, (R)-1-($R_p$)-2-[2-(diphenylphosphino)-phenyl]-ferrocenyl-ethylbis[3,5-bis (trifluoromethyl)phenyl]phosphine.

39. The process of any of items 30 to 38, wherein in step (b) the at least one ligand is present in an amount of 3-25 mol %, particularly of 5-20 mol %, and more particularly 8-15 mol %, with respect to the intermediate of formula II.

40. The process of any of items 30 to 38, wherein in step (b) the suitable solvent is selected from tetrahydrofuran (THF), dimethylformamide (DMF), toluene, MeOH, water, 2-methyltetrahydrofuran, and any combination thereof, and is particularly THF.

41. The process of any of items 30 to 40, wherein in step (b) the reaction is carried out at a temperature of 25° C. to 80° C., particularly from 30° C. to 70° C., and more particularly about 60° C.

42. The process of any of the preceding items, wherein the intermediate of formula III is as defined in any of items 85 to 95.

43. The process of any of the preceding items, wherein in step (c) the intermediate of formula III is converted to the intermediate of formula I by an amination process.

44. The process of item 43, wherein the amination process in step (c) comprises or consists the steps of:
   (c1) reacting the intermediate of formula III with an organo-zinc compound and/or an organo-magnesium compound in a suitable solvent, and
   (c2) reacting with an electrophilic aminating reagent in a suitable solvent.

45. The process of item 44, wherein in step (c1) the organo-zinc compound is selected from the group consisting of zinc compounds with two alkyl residues, wherein the alkyl residues having from 1 to 12 carbon atoms, and wherein the organo-zinc compound is particularly diethylzinc, dimethylzinc, methylzinc chloride, ethylzinc chloride or any combination thereof.

46. The process of item 44, wherein in step (c1) the organo-magnesium compound is selected from the group consisting of methylmagnesium chloride, ethylmagnesium chloride, isopropylmagnesium chloride, cycloalkylmagnesium chloride, and any combination thereof, and is particularly methylmagnesium chloride or ethylmagnesium chloride.

47. The process of item 44 or 45, wherein in step (c1) the organo-zinc compound is present in an amount of 1.0 to 2.0 equivalents, particularly of 1.05 to 1.2 equivalents, and more particularly about 1.1 equivalents, with respect to the compound of formula III.

48. The process of item 44 or 45, wherein in step (c1) the organo-magnesium compound is present in an amount of 2.0 to 2.5 equivalents, particularly of 2.1 to 2.3 equivalents, and more particularly about 2.2 equivalents, with respect to the compound of formula III.

49. The process of any of items 44 to 48, wherein in step (c1) the suitable solvent is selected from aprotic solvents.

50. The process of any of items 44 to 49, wherein in step (c1) the suitable solvent is selected from THF, toluene, hexane, heptane, diglyme, 2-methyltetrahydrofuran, and any combination thereof, and is particularly THF.

51. The process of any of items 44 to 50, wherein step (c1) is carried at a temperature of −15° C. to 25° C., particularly from −5° C. to 5° C., and more particularly 0° C.

52. The process of any of items 44 to 51, wherein in step (c2) the electrophilic aminating reagent is selected from the group consisting of monochloramine, hydroxylamine-O-sulfonicacid, N-chloro tosylamide sodium salt, benzylchloroamine, phenylethanechloroamine, O-mesitylenesulphonyl-hydroxylamine, N-α-methybenzylchloroamine, O-benzyl-N-chlorohydroxylamine, N-benzyl-1-phenylethylchloramine, and any combination thereof.

53. The process of any of items 44 to 52, wherein in step (c2) the electrophilic aminating reagent is present in an amount of more than 1 equivalent, particularly of 2.0 to 3.5 equivalents, more particularly of 2.1 to 3.4 equivalents, and most particularly of 2.2 to 3.2 equivalents, with respect to the intermediate of formula III.

54. The process of any of items 44 to 53, wherein in step (c2) the suitable solvent is selected from THF, toluene, hexane, heptane, diglyme, 2-methyltetrahydrofuran, and any combination thereof, and is particularly THF.

55. The process of any of items 44 to 54, wherein step (c2) is carried out at a temperature of 20° C. to 30° C., particularly from 20° C. to 25° C., and more particularly at room temperature.

56. The process of item 43, wherein the amination process in step (c) comprises or consist the steps of:
 (c3) reacting the intermediate of formula III with a haloboron agent and/or a bifluoride agent, and
 (c4) reacting with an azide aminating reagent.

57. The process of item 56, wherein the halo-boron agent is selected from boron trichloride, boron triiodide, and boron tribromide, and any combination thereof, and is particularly boron trichloride.

58. The process of item 56, wherein the bifluoride agent is selected from potassium hydrogen bifluoride, ammonium hydrogen bifluoride, sodium hydrogen bifluoride, and any combination thereof, and is particularly potassium hydrogen bifluoride.

59. The process of item 56, wherein the azide aminating reagent is selected from the group consisting of alkyl azides and aryl azides, and is particularly benzyl azide, tosylazide, benzoylazide, or acetylazide.

60. The process of any of items 1 to 42, wherein step (c) comprises or consist the steps of:
 (c5) reacting the intermediate of formula III with an oxidation agent in a suitable solvent to obtain the intermediate of formula IV

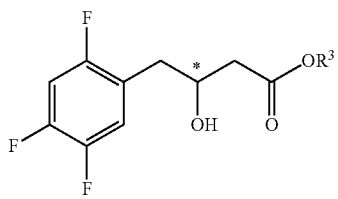

(IV)

wherein the stereogenic center marked with an * is either in (R)- or (S)-configuration at marked center, or it is in racemic form, and
wherein $R^3$ is selected from alkyl residues having from 1 to 6 carbon atoms; and
 (c6) reacting the intermediate of formula IV with an aminating agent to obtain an intermediate of formula I.

61. The process of item 60, wherein the oxidation agent in step (c5) is selected from the group consisting of sodium perborate hydrate, hydrogen peroxide, sodium hypochlorite, sodium percarbonate, sodium bromate, potassium bromate, sodium chlorate, potassium chlorate, oxone, and any combination thereof.

62. The process of item 60 or 61, wherein the oxidation agent in step (c5) is present in an amount of 1.0 to 5.5 equivalents, particularly of 1.8 to 5.0 equivalents, and more particularly of 2.0 to 4.0 equivalents, with respect to the intermediate of formula III.

63. The process of any of items 60 to 62, wherein in step (c5) the suitable solvent is selected from THF, water, methanol, acetonitrile, ethylacetate, isopropylacetate, ethanol, propanole, 2-methyltetrahydrofuran, and any combination thereof.

64. The process of any of items 60 to 63, wherein step (c5) carried at a temperature of 15° C. to 30° C., particularly from 20° C. to 25° C., and more particularly at room temperature.

65. The process of any of items 60 to 64, wherein in step (c6) the aminating agent is selected from ammonia, alkyl amines, aryl amines, aryl-alkyl amines, alkyl nitriles, aryl nitriles, and any combination thereof, wherein the amines are particularly selected from benzylamine, p-methoxyaniline, 3,4-dimethoxybenzylamine tosylamine, O-benzylhydroxylamine, O-methyl-hydroxylamine, dimethylamine, dibenzylamine, and N-α-methylbenzylamine, N-benzyl-1-phenylethylamine, N-bis[α-methylbenzyl]amine; and wherein the nitriles are particularly selected from acetonitrile, benzonitrile, chloroacetonitrile, phenylacetonitrile, acrylonitrile, isopropylnitrile, 2-methylbutyronitrile, mandelonitrile, and 2-methoxy-2-phenylacetonitrile.

66. The process of any of items 60 to 65, wherein in step (c6) the aminating agent is selected from ammonia, alkyl amines, aryl amines, and aryl-alkyl amines, and is present in an amount of 1.0 to 3 equivalents, and particularly about 1.0 to 2.0 equivalent, with respect to the intermediate of formula IV.

67. The process of any of items 60 to 65, wherein in step (c6') the aminating agent is selected from alkyl nitriles, and aryl nitriles, and is present in an amount of 2.5 to 10 equivalents, particularly of 4 to 8 equivalents, and more particularly about 5 to 7.5 equivalents with respect to the intermediate of formula IV.

68. The process of any of items 60 to 66, wherein step (c6) is transition metal catalyzed process, particularly a transition metal catalyzed process using a catalyst comprising a transition metal compound and optionally at least one ligand.

69. The process of item 68, wherein in step (c6) the transition metal compound is selected from a gold compound, particularly Au/TiO$_2$; a rhodium compound, particularly Cp*RhCl$_2$dimer; an iron compound, particularly FeBr$_3$, FeCl$_3$; an iridium compound, particularly IrCl(cod)$_2$dimer, Cp*IrCl$_2$dimer, Cp*IrBr$_2$dimer or Cp*IrI$_2$dimer; and a ruthenium compound, particularly Ru(p-cymene)Cl$_2$dimer, Ru(p-cymene)Cl$_2$dimer, Ru(p-cymene)Cl$_2$dimer or Ru$_3$CO$_{12}$.

70. The process of item 68 or 69, wherein in step (c6) the transition metal compound is present in an amount of 1-15 mol %, particularly of 2-7.5 mol %, and more particularly 3.5-5.5 mol %, to the intermediate of formula IV.

71. The process of any of items 68 to 70, wherein in step (c6) the optionally at least one ligand is selected from monophosphine ligands, diphosphine ligands, amine type ligands, and any combination thereof.

72. The process of any of items 68 to 71, wherein in step (c6) the optionally at least one ligand is selected from monophosphine ligands, and is particularly triphenylphosphine, 2-dicyclohexylphosphino-1-phenyl-1H-pyrole, trimethylphosphine, neomethyldiphenylphosphine, tricyclohexylphosphine, tributylphosphine, and any combination thereof.

73. The process of any of items 68 to 71, wherein in step (c6) the optionally at least one ligand is selected from diphosphine ligands, and is particularly 1,2-bis(diphenyl-phosphino)benzene, 1,1,-bis(di-tert-butylphosphino)ferrocene, (oxydi-2,1-phenylene)bis-(diphenylphosphine), (R)-2,2-bis(diphenylphosphino)-1,1-binaphthalene, (S)-2,2-bis(diphenylphosphino)-1,1-binaphthale, (S,R)-(diphenylphosphino)-ferrocenyl-ethyldi-tert-butylphosphin, (R,S)-(diphenylphosphino)-ferrocenyl-ethyldi-tert-butylphosphin, 1,3-bis(diphenylphosphino)propane, 2,2-bis(diphenylphosphino)-1,1-binaphthyl, and any combination thereof; or wherein in step (c6) the optionally at least one ligand is selected from amine type ligands selected from (D)-pyroglutamic acid, (L)-pyroglutamic acid, (D)-proline intermediates, (L)-proline intermediates, (D)-methyl-N-phenylcarbamate, (L)-methyl-N-phenylcarbamate, (D)-N-phthaloylglycine, (L)-N-phthaloylglycine, (D)-glutamic acid, and (L)-glutamic acid.

74. The process of any of items 68 to 73, wherein the transition metal catalyzed process is optionally carried out in the presence of a base, particularly wherein the base is selected from $NaHCO_3$, $KHCO_3$, KOH, NaOH, NaOt-Bu, KOt-Bu, $K_3PO_4$, and any combination thereof, more particularly $NaHCO_3$.

75. The process of item 74, wherein the base is present in an amount of 1-15 mol %, particularly of 3-12 mol %, and more particularly 5-10 mol %, with respect to the intermediate of formula IV.

76. The process of any of items 68 to 75, wherein in step (c6) the optionally at least one ligand is present in an amount of 1-15 mol %, particularly of 2-7.5 mol %, and more particularly 3.5-5.5 mol %, to the intermediate of formula IV 77. The process of any of items 60 to 65 and 67, wherein step (c6') is an acid catalyzed process.

78. The process of item 77, wherein in step (c6') the acid is selected from Brønsted acids, and is particularly trifluoromethanesulfonic acid (HOTf), methanesulfonic acid, p-toluenesulfonic acid (PTSA), chlorsulfonic acid, 2,5-dinitrobenzenesulfonic acid (DNBSA), sulfuric acid or dodecylbenzenesulfonic acid (DBSA), and is most particularly HOTf.

79. The process of item 77 or 78, wherein in step (c6') the acid is present in an amount of 0.15-15 equivalents, particularly of 1-10 equivalents, and more particularly 5-7.5 equivalents, to the intermediate of formula IV.

80. The process of item 1, wherein $R^4$ and $R^5$ are hydrogen and the process comprises or consists the steps of:
(a) providing an intermediate of formula II, preferably by a process as defined in any of items 103 to 120,

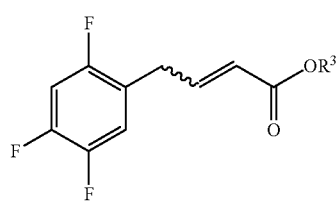

(II)

(b) reacting the intermediate of formula II, wherein $R^3$ is selected from alkyl residues having from 1 to 6 carbon atoms with
a. bis(pinacolato)diboron, preferably present in an amount of 1.1-1.3 equivalents, more preferably about 1.1 equivalents,
b. in the presence of copper(I) chloride, preferably present in an amount of 4-12 mol %, more preferably about 10 mol %;
c. mono- and/or diphosphine ligands, preferably present in an amount of 4-12 mol %, more preferably 8-10 mol %, and
d. optionally NaOt-Bu, preferably present in an amount of 10-20 mol %, more preferably about 15 mol %,
each to the intermediate of formula II, in THF at a temperature of 20° C. to 25° C., preferably at room temperature,
to obtain an intermediate of formula III,

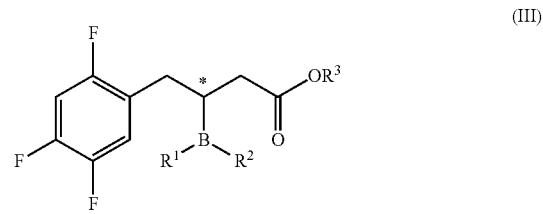

(III)

wherein $R^1$ and $R^2$ form a pinacolato group and $R^3$ is selected from alkyl residues having from 1 to 6 carbon atoms;

(c) reacting the intermediate of formula III with
e. methylmagnesium chloride, preferably present in an amount of 1.8 to 2.3 equivalents, more preferably about 2.0 equivalents,
with respect to the intermediate of formula III, in THF at a temperature of −3° C. to 3° C., preferably at about 0° C.; and with
f. monochloramine, preferably present in an amount of 2.0 to 3.5 equivalents, more preferably about 3.2 equivalents, and/or
g. hydroxylamine-O-sulfonic acid, preferably present in an amount of 2.0 to 3.5 equivalents, more preferably about 2.2 equivalents,
each with respect to the intermediate of formula III, in THF and water at a temperature of 20° C. to 25° C., preferably at room temperature,
to obtain the intermediate of formula I.

81. The process of item 1, wherein $R^4$ and W are alkoxycarbonyl residues optionally chiral, having from 2 to 13 carbon atoms, aryloxycarbonyl residues optionally chiral, having from 7 to 25 carbon atoms; and the process comprises or consists the steps of:
(a) providing an intermediate of formula II as defined in any of items 103 to 120,

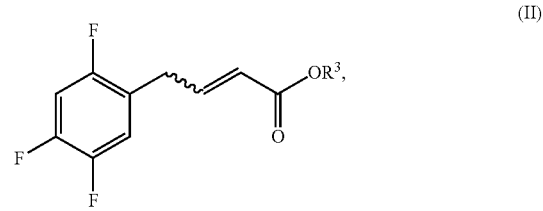

(II)

wherein $R^3$ is selected from alkyl residues having from 1 to 6 carbon atoms;
(b) reacting the intermediate of formula II with a borating agent in a suitable solvent to obtain an intermediate of formula III,

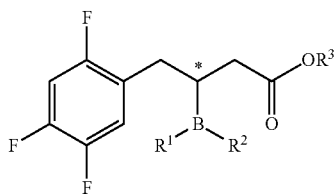

(III)

wherein the stereogenic center marked with an * is either in (R)- or (S)-configuration at marked center, or it is in racemic form, and wherein $R^1$ and $R^2$ are identical or different, and are selected from (i) alkyl or alkoxy residues, each having from 1 to 12 carbon atoms, wherein each alkyl or alkoxy residue is optionally aryl substituted, (ii) aryl or aryloxy residues, each having from 6 to 14 carbon atoms, wherein each aryl or aryloxy residue is optionally alkyl substituted;

(iii) halides; and (iv) wherein $R^1$ and $R^2$ optionally form a chiral or non-chiral 5 to 10, particularly 5 to 6, membered mono or bicyclic ring, wherein the ring is optionally substituted at least one position with an alkyl residue having from 1 to 12 carbon atoms and/or an aryl residue having from 6 to 14 carbon atoms, and wherein $R^1$ and $R^2$ optionally form an O-benzenedioxy residue; and $R^3$ is selected from alkyl residues having from 1 to 6 carbon atoms; and (c) converting the intermediate of formula III to the intermediate of formula I, wherein step (c) comprises the steps of:

(c5) reacting the intermediate of formula III with an oxidation agent in a suitable solvent to obtain the intermediate of formula IV

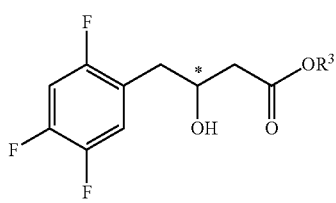

(IV)

wherein the stereogenic center marked with an * is either in (R)- or (S)-configuration at marked center, or it is in racemic form, and wherein $R^3$ is same as above; and (c6') reacting the intermediate of formula IV with an aminating agent, alkyl nitriles, aryl nitriles, each having a formula Xa or Xb, $R^4CN$ (Xa)

$R^5CN$ (Xb)

wherein $R^4$ and $R^5$, wherein are same as above to obtain an intermediate of formula I',

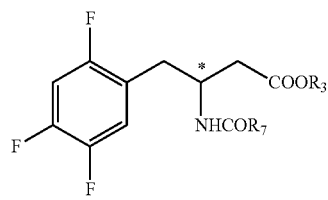

(I')

wherein the stereogenic center marked with an * is either in (R)- or (S)-configuration at marked center, or it is in racemic form and wherein $R^3$ is selected from alkyl residues having from 1 to 6 carbon atoms; and $R^7$ is selected from alkyl residues having from 1 to 6 carbon atoms and aryl residues, having from 6 to 24 carbon atoms, optionally substituted.

and wherein step (b) and step (c5) occur in one-pot.

82. The process of item 1, wherein $R^4$ and $R^5$ are different, and are independently selected from (i) hydrogen;

(ii) alkyl residues optionally chiral, having from 1 to 12 carbon atoms, wherein the alkyl residues are optionally aryl and/or aryloxy substituted;

(iii) alkyloxy residues optionally chiral, having from 1 to 12 carbon atoms, wherein the alkyloxy residues are optionally aryl substituted;

(iv) aryl residues optionally chiral, having from 6 to 24 carbon atoms, wherein the aryl residues are optionally alkyl and/or alkyloxy substituted;

(v) aryloxy residues optionally chiral, having from 6 to 24 carbon atoms, wherein the aryloxy residues are optionally alkyl substituted;

(vi) benzyl;

(vii) alkaloyl residues optionally chiral, having from 2 to 13 carbon atoms, wherein the alkaloyl residues are optionally aryl substituted;

(viii) aroyl residues optionally chiral, having from 7 to 25 carbon atoms, wherein the aryloxy residues are optionally alkyl substituted; and (ix) alkoxycarbonyl residues optionally chiral, having from 2 to 13 carbon atoms;

(x) aryloxycarbonyl residues optionally chiral, having from 7 to 25 carbon atoms; and (xi) tosyl;

and particularly $R^4$ is hydrogen and $R^5$ is tosyl, or $R^4$ is hydrogen and $R^5$ is tosyl, or, $R^4$ is hydrogen and $R^5$ is benzyl, or $R^4$ is hydrogen and $R^5$ is O-benzyl, or $R^4$ is hydrogen and $R^5$ is O-methyl, or $R^4$ is benzyl and $R^5$ is N-α-methylbenzyl, or $R^4$ is hydrogen and $R^5$ is tert-butyl-oxy-carbonyl, or $R^4$ is hydrogen and $R^5$ is benzyl-oxy-carbonyl, or $R^4$ is hydrogen and $R^5$ is benzoyl, or $R^4$ is hydrogen and $R^5$ is acetyl, or $R^4$ is hydrogen and $R^5$ is N-α-methylbenzyl, or R[4] is hydrogen and R[5] is phenyl-O-methyl;
the process comprises or consists the steps of:
(a) providing an intermediate of formula II, preferably by a process as defined in any of items 103 to 120,

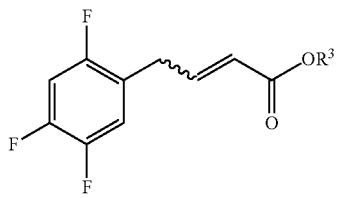

(II)

(b) reacting the intermediate of formula II with
(i) bis(pinacolato)diboron, preferably present in an amount of 1.1-1.3 equivalents, more preferably about 1.1 equivalents,
(ii) in the presence of copper(I) chloride, preferably present in an amount of 4-12 mol %, more preferably about 10 mol %;
(iii) mono- and/or diphosphine ligands, preferably present in an amount of 4-12 mol %, more preferably 8-10 mol %, and
(iv) optionally NaOt-Bu, preferably present in an amount of 10-20 mol %, more preferably about 15 mol %,
each with respect to the intermediate of formula II, in THF at a temperature of 20° C. to 25° C., preferably at room temperature,
to obtain an intermediate of formula III,

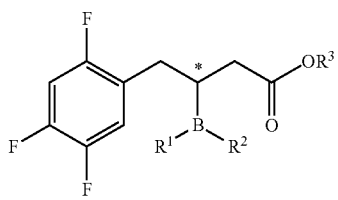

(III)

wherein the stereogenic center marked with an * is either in (R)- or (S)-configuration at marked center, or it is in racemic form, and
wherein R[1] and R[2] form a pinacolato group and wherein R[3] is selected from alkyl residues having from 1 to 6 carbon atoms;
(c) reacting the intermediate of formula III with
(i) sodium perborate hydrate, preferably present in an amount of 1.8 to 5.0 equivalents, more preferably about 4.0 equivalents, with respect to the intermediate of formula III in THF and water, and/or
(ii) aqueous hydrogen peroxide, preferably present in an amount of 1.8 to 5.0 equivalents, more preferably about 2.0 equivalents, with respect to the intermediate of formula III in THF and water, and/or
(iii) sodium hypochlorite in an aqueous solution, preferably present in an amount of 1.8 to 5.0 equivalents, more preferably about 1.5 equivalents;

with respect to the intermediate of formula III, in methanol and water, at a temperature of 20° C. to 25° C., preferably at room temperature,
to obtain the intermediate of formula IV

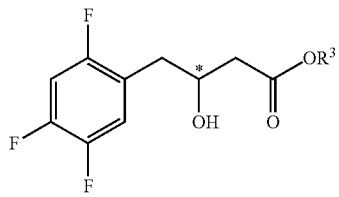

(IV)

wherein the stereogenic center marked with an * is either in (R)- or (S)-configuration at marked center, or it is in racemic form, and R[3] is selected from alkyl residues having from 1 to 6 carbon atoms;
(d) reacting the intermediate of formula IV with an aminating agent to obtain an intermediate of formula I.
83. The process of item 82, wherein the steps (b) and (c) occur in one-pot.
84. An intermediate of formula I', and the isomers, and the isomer mixtures thereof

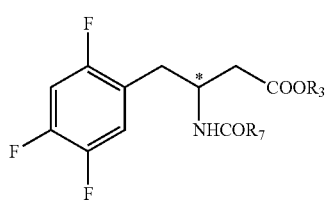

(I')

wherein the stereogenic center marked with an * is either in (R)- or (S)-configuration at marked center, or it is in racemic form and
wherein R[3] is selected from alkyl residues having from 1 to 6 carbon atoms; and R[7] is selected from alkyl residues having from 1 to 6 carbon atoms and aryl residues, having from 6 to 24 carbon atoms optionally substituted.
85. An intermediate of formula III, and the isomers, and the isomer mixtures thereof

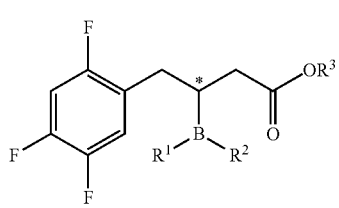

(III)

wherein R[1] and R[2] are identical, and are selected from
(i) alkyl or alkoxy residues, each having from 1 to 12 carbon atoms, wherein each alkyl or alkoxy residue is optionally aryl substituted;
(ii) aryl or aryloxy residues, each having from 6 to 14 carbon atoms, wherein each aryl or aryloxy residue is optionally alkyl substituted;
(iii) halides; and
(iv) wherein R[1] and R[2] optionally form a chiral or non-chiral 5 to 10, particularly 5 to 6, membered mono or bicyclic ring, wherein the ring is optionally substituted at least one position with an alkyl residue having from 1 to 12 carbon atoms and/or an aryl residue having from 6 to 14 carbon atoms, and wherein R¹ and R² optionally from a O-benzenedioxy residue; and R³ is selected from alkyl residues having from 1 to 6 carbon atoms.

86. The intermediate of item 85, wherein the alkyl or alkyloxy residues each have from 1 to 5 carbon atoms, particularly 1 to 3 carbon atoms.

87. The intermediate of item 85, wherein the aryl or aryloxy residues each have from 6, 7 or 14 carbon atoms.

88. The intermediate of item 85 or 86, wherein the alkyl or alkoxy residues are aryl substituted.

89. The intermediate of item 85 or 87, wherein the aryl or aryloxy residues are alkyl substituted.

90. The intermediate of item 88, wherein R¹ and R² form a 5 to 6 membered ring.

91. The intermediate of item 88 or 90, wherein R¹ and R² form a chiral ring.

92. The intermediate of item 85 or 90, wherein R¹ and R² form a non-chiral ring.

93. The intermediate of item 85 or 90, wherein R¹ and R² are a halide selected from chloride, bromide and iodide, and are particularly chloride.

94. The intermediate of item 85, wherein R¹ and R² form a chiral or non-chiral 5 to 10 membered mono or bicyclic ring, wherein the ring is substituted at least one position with an alkyl residue having from 1 to 12 carbon atoms and/or an aryl residue having from 6 to 14 carbon atoms, and wherein R¹ and R² optionally from a O-benzenedioxy residue.

95. The intermediate of item 85, having the formula

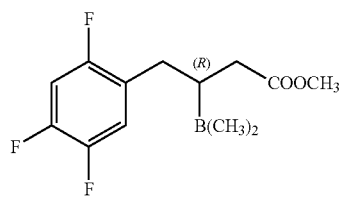

(IIIa)

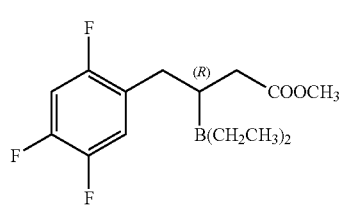

(IIIb)

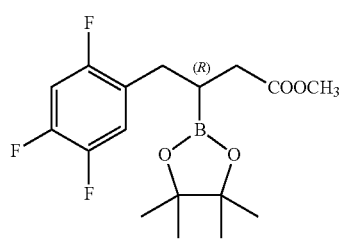

(IIIc)

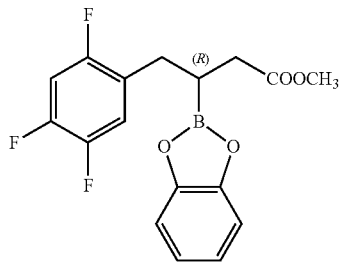

(IIId)

96. An intermediate of formula III as defined in any of items 85 to 90, as obtained or obtainable by a process as defined in any of items 1 to 42.

97. Use of an intermediate of formula II in a process for the preparation of an intermediate of formula III as defined in any of items 85 to 95.

98. Use of intermediates according to any of items 84 to 95 in a process for the preparation of (R)-3-Amino-1-[3-(trifluormethyl)-5,6,7,8-tetrahydro[1,2,4]triazol[4,3-a]pyrazin-7-yl]-4-(2,4,5-trifluorphenyl)butan-1-on.

99. Use of an intermediate according to any of items 85 to 95 in a process for the preparation of an intermediate of formula I as defined in any of items 1 to 7.

100. Use of an intermediate according to any of items 85 to 95 in a process for the preparation of an intermediate of formula I as defined in any of items 1 to 7, wherein the intermediate of formula I is used in a process for the preparation of (R)-3-Amino-1-[3-(trifluormethyl)-5,6,7,8-tetrahydro[1,2,4]triazol[4,3-a]pyrazin-7-yl]-4-(2,4,5-trifluorphenyl)butan-1-on.

101. Use of an intermediate according to any of items 85 to 95 in a process for the preparation of an intermediate of formula IV.

102. Use of an intermediate according to any of items 85 to 95 in a process for the preparation of an intermediate of formula IV, wherein the intermediate of formula IV optionally is used in a process for the preparation of an intermediate of formula I as defined in any of items 1 to 7, wherein the intermediate of formula I is optionally used in a process for the preparation of (R)-3-Amino-1-[3-(trifluormethyl)-5,6,7,8-tetrahydro[1,2,4]triazol[4,3-a]pyrazin-7-yl]-4-(2,4,5-trifluorphenyl)butan-1-on.

103. A process for the preparation of an intermediate of formula II

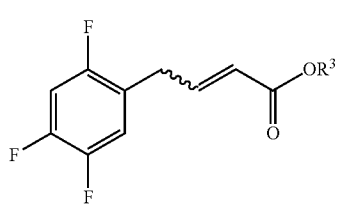

(II)

wherein R³ is selected from alkyl residues having from 1 to 6 carbon atoms;
the process comprises or consists the steps of:
(a) providing an intermediate of formula V

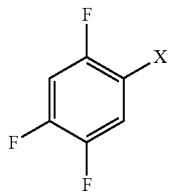

(V)

(b) reacting the intermediate of formula V, wherein X is selected from Cl, Br, I, and is preferably Br with a Grignard compound or with magnesium in the presence of an activating agent, wherein the activating agent is particularly selected from iodine, methyl iodide, 1,2-dibromoethane, and any combination thereof;
in a suitable solvent to obtain an intermediate of formula VI

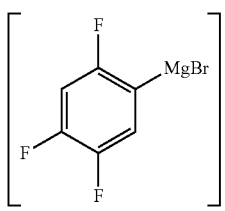

(VI)

(c) reacting the intermediate of formula VI with a compound of formula VII

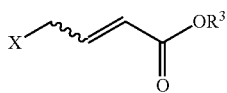

(VII)

wherein X is selected from Cl, Br, and I, and is preferably Br,
wherein R³ is same as above;
in a metal catalyzed cross-coupling process in a suitable solvent to obtain the intermediate of formula II.
104. The process of item 103, wherein in step (b) the Grignard compound has the formula R⁶MgX, wherein X is selected from Cl, Br or I, and particularly wherein R⁶ is an alkyl residue having from 1 to 6 carbon atoms.
105. The process of item 103 or 104, wherein in step (b) the Grignard compound is selected from the group consisting of i-PrMgCl, MeMgCl, s-BuMgCl, i-PrMgCl.LiCl complex, s-BuMgCl.LiCl complex, and any combination thereof, and is particularly i-PrMgCl.
106. The process of any of items 103 to 106, wherein in step (b) the Grignard compound is present in an amount of 1.1 to 1.5 equivalents, particularly of 1.2-1.3 equivalents and more particularly about 1.2 equivalents, with respect to the compound of formula V.
107. The process of any of items 103 to 106, wherein in step (b) the suitable solvent is selected from THF, toluene, methyl-tert-butylether, diethylether, 2-methyltetrahydrofuran, and any combination thereof, and is particularly THF.
108. The process of any of items 103 to 107, wherein in step (b) the suitable solvent is preferably substantially water-free.
109. The process of any of items 103 to 108, wherein in step (b) the reaction is carried out at a temperature of –30° C. to –15° C., particularly of –25° C. to –18° C. and more particularly about –20° C.
110. The process of any of items 103 to 109, wherein in step (c) the metal catalyzed cross-coupling process is carried out using a catalyst comprising a metal compound, wherein the metal compound is preferably selected from a cobalt (II) compound, a cobalt(III) compound, an iron(III) compound, an iron(II) compound and a manganese(II) compound.
111. The process of items 110, wherein the metal compound is selected from cobalt(II) bromide, iron(III) acetylacetonate, iron(II) acetyacetonate, cobalt(III) acetylacetonate, cobalt(II) acetylacetonate and manganese(II) acetylacetonate.
112. The process of item 110 or 111, wherein in step (c) the metal compound is present in an amount of 2-25 mol %, particularly of 4-20 mol % and more particularly 7-15 mol %, with respect to the intermediate of formula VII.
113. The process of any of items 109 to 112, wherein in step (c) the metal catalyzed cross-coupling process is carried out in the presence of an additive.
114. The process of item 113, wherein in step (c) the additive is chelating agent for transition metal catalyst.
115. The process of item 113 or 114, wherein the additive is selected from tetramethylethylenediamine (TMEDA), hexamethylenetetramin (HMTA), 1,2-dimethoxyethane, DABCO, and any combination thereof.
116. The process of any of items 113 to 115, wherein the additive in step (c) is present in an amount of 2-40 mol %, particularly of 3-35 mol %, and more particularly 5-30 mol %, with respect to the intermediate of formula VII.
117. The process of any of items 103 to 116, wherein in step (c) the suitable solvent is selected from aprotic solvents.
118. The process of any of items 103 to 117, wherein in step (c) the suitable solvent is selected from THF, diethylether, 2-methyltetrahydrofuran, methyl-tert-butylether, and any combination thereof.
119. The process of any of items 103 to 118, wherein in step (c) the reaction is carried out at a temperature of –25° C. to 5° C., particularly from –15° C. to –5° C., and more particularly about 0° C.
120. The process of item 103,
the process comprising or consisting the steps of
(a) providing an intermediate of formula V

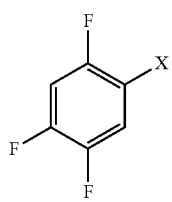

(V)

(b) reacting the intermediate of formula V with i-PrMgCl, preferably present in an amount of 1.1 to 1.5 equivalents, more preferably about 1.2 equivalents, with respect to the intermediate of formula V in THF at a temperature of –5° C. to –15° C., particularly from –30° C. to –15° C., and more particularly about –25° C.,

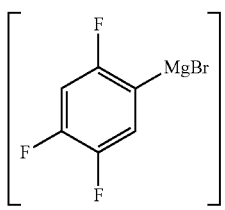

(c) reacting the intermediate of formula VI with a compound of formula VIIa

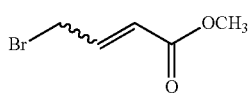

in the presence of
(i) cobalt(II) bromide, preferably present in an amount of 4-12 mol %, more preferably about 6 mol %, or
(ii) iron(III) acetylacetonate, preferably present in an amount of 4-12 mol %, more preferably about 10 mol %, and most preferably about 15 mol %
(iii) optionally TMEDA, preferably present in an amount of 5-35 mol %, more preferably 15-30 mol %, and
(iv) optionally HMTA, preferably present in an amount of 8-25 mol %, more preferably about 15 mol %,
each with respect to the intermediate of formula VIIa in THF at a temperature of −25° C. to 5° C., preferably at 0° C., to obtain the intermediate of formula II.

The invention claimed is:
1. A process for the preparation of an intermediate of formula I

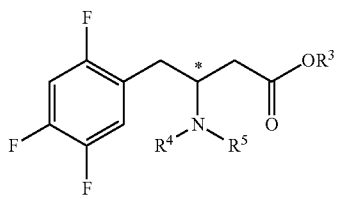

wherein the stereogenic center marked with an * is either in (R)- or(S)-configuration at marked center, or it is in racemic form, and
wherein $R^4$ and $R^5$ are identical or different, and are independently selected from
(i) hydrogen;
(ii) alkyl residues optionally chiral, having from 1 to 12 carbon atoms, wherein the alkyl residues are optionally aryl and/or aryloxy substituted;
(iii) alkyloxy residues optionally chiral, having from 1 to 12 carbon atoms, wherein the alkyloxy residues are optionally aryl substituted;
(iv) aryl residues optionally chiral, having from 6 to 24 carbon atoms, wherein the aryl residues are optionally alkyl and/or alkyloxy substituted;
(v) aryloxy residues optionally chiral, having from 6 to 24 carbon atoms, wherein the aryloxy residues are optionally alkyl substituted;
(vi) benzyl;
(vii) alkaloyl residues optionally chiral, having from 2 to 13 carbon atoms, wherein the alkaloyl residues are optionally aryl substituted;
(viii) aroyl residues optionally chiral, having from 7 to 25 carbon atoms, wherein the aryloxy residues are optionally alkyl substituted; and
(ix) alkoxycarbonyl residues optionally chiral, having from 2 to 13 carbon atoms;
(x) aryloxycarbonyl residues optionally chiral, having from 7 to 25 carbon atoms; and
(xi) tosyl;
wherein $R^3$ is selected from alkyl residues having from 1 to 6 carbon atoms;
the process comprising the steps of:
(a) providing an intermediate of formula II,

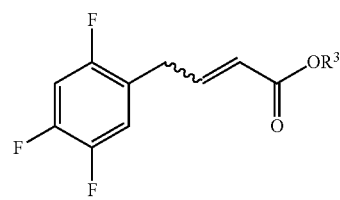

(b) reacting the intermediate of formula II with a borating agent in a suitable solvent to obtain an intermediate of formula III,

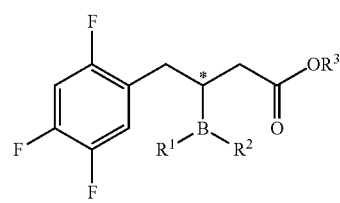

wherein the stereogenic center marked with an * is either in (R)- or (S)-configuration at marked center, or it is in racemic form, and
wherein $R^1$ and $R^2$ are identical or different, and are selected from (i) alkyl or alkoxy residues, each having from 1 to 12 carbon atoms, wherein each alkyl or alkoxy residue is optionally aryl substituted,
(ii) aryl or aryloxy residues, each having from 6 to 14 carbon atoms, wherein each aryl or aryloxy residue is optionally alkyl substituted;
(iii) halides; and
(iv)wherein $R^1$ and $R^2$ optionally form a chiral or non-chiral 5 to 10, membered mono or bicyclic ring, wherein the ring is optionally substituted at least one position with an alkyl residue having from 1 to 12 carbon atoms and/or an aryl residue having from 6 to 14 carbon atoms, and wherein $R^1$ and $R^2$ optionally form an O-benzenedioxy residue;

and wherein $R^3$ is same as above;
(c) converting the intermediate of formula III to the intermediate of formula I.

2. The process of claim 1, wherein the intermediate of formula I is

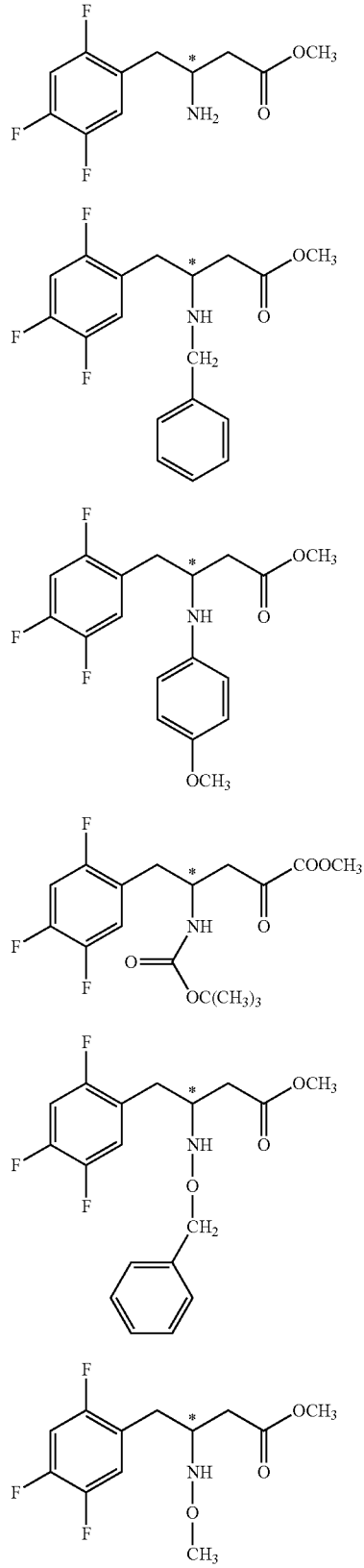

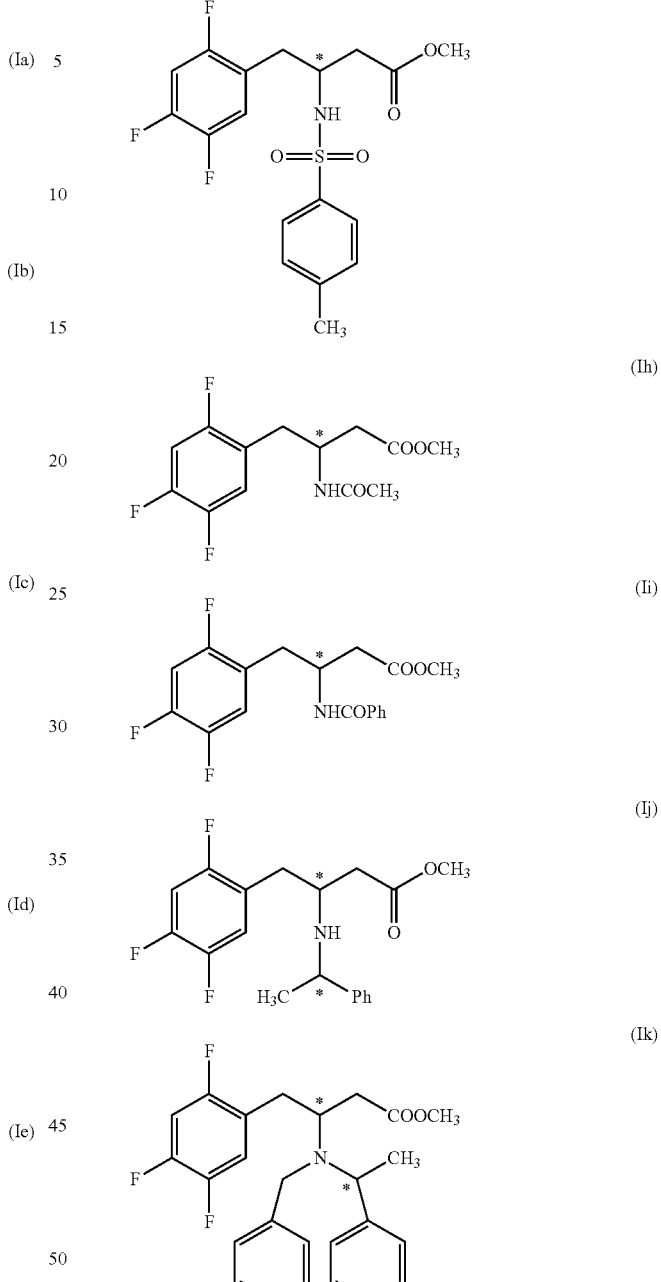

wherein the stereogenic center marked with an * is either in (R)- or(S)-configuration at marked center, or it is in racemic form.

3. The process of claim 1, wherein step (b) is a transition metal catalyzed process using a catalyst comprising a transition metal compound or a catalyst comprising transition metal compound and at least one ligand, wherein the transition metal compound is selected from the group consisting of copper(I) chloride, copper(II) bromide, copper(I) iodide, copper(I) oxide, copper(II) oxide, copper(I) acetate, copper (II) triflate, copper(II) carbonate, and any combination thereof.

4. The process of claim 3, wherein in step (b) the suitable solvent is selected from tetrahydrofuran (THF), dimethylformamide (DMF), toluene, water, 2-methyltetrahydrofuran, and any combination thereof.

5. The process of claim 3, wherein in step (b) the transition metal compound is copper(II) carbonate and the suitable solvent is water.

6. The process of claim 3, wherein step (b) is a transition metal catalyzed process that further comprises a ligand selected from monophosphine ligands selected from triphenylphosphine, trimethylphosphine, tricyclohexylphosphine, tributylphosphine, tri-(o-tolyl)-phosphine, tri-(2-furyl)phosphine, tris(dimethylamino)-phosphine, tribenzylphosphine, tripyrolydinophosphine, tris(4-methoxyphenyl)phosphine and any combination thereof; diphosphine ligands selected from 1,2-bis(diphenyl-phosphino)benzene, 1,1,-bis(di-tert-butylphosphino)ferrocene, (oxydi-2,1-phenylene)bis-(diphenylphosphine), and any combination thereof; and N,O-containing ligand.

7. The process of claim 6, wherein the ligand in step (b) is chiral selected from (R)-2,2'-bis(diphenylphosphino)-1,1-binaphthalene, (S)-2,2'-bis(diphenylphosphino)-1,1-binaphthalene, (S,R)-(diphenylphosphino)-ferrocenyl-ethyldi-tert-butylphosphine, (R,S)-(diphenylphosphino)-ferrocenyl-ethyldi-tert-butylphosphine, (S)-1-($S_p$)-2[2-(diphenylphosphino)-phenyl]ferrocenyl-ethylbis[3,5-bis(trifluoromethyl)phenyl]phosphine, (R)-1 -($R_p$)-2-[2-(diphenylphosphino)-phenyl]-ferrocenyl-ethylbis[3,5-bis(trifluoromethyl)phenyl]phosphine, (S)-4-tert-butyl-2-[($S_p$)-2-(diphenylphosphino)ferrocenyl]-2-oxazoline, (R)-4-tert-butyl-2-[($S_p$)-2-(diphenylphosphino)ferrocenyl]-2-oxazoline, (1S,1'S)-1,1'-bis[bis[3,5-bis(trifluoromethyl)phenyl]phosphino]-2,2'-bis[(S)-dimethylamino)phenylmethyl], (1R,1'R)-1,1'-bis[bis[3,5-bis(trifluoromethyl)phenyl]phosphino]-2,2'-bis[(R)-(dimethylamino)phenylmethyl], and any combination thereof.

8. The process of claim 1, wherein step (b) is a transition metal free catalyzed process using a base and at least one ligand, wherein the base is selected from cesium carbonate, cesium hydroxide, cesium phosphate, cesium chloride, cesium fluoride, cesium iodide, and any combination thereof.

9. The process of claim 1, wherein in step (c) the intermediate of formula III is converted to the intermediate of formula I by an amination process.

10. The process of claim 9, wherein the amination process in step (c) comprises the steps of:
(c1) reacting the intermediate of formula III with an organo-zinc compound and/or an organo-magnesium compound in a suitable solvent, and
(c2) reacting with an electrophilic aminating reagent in a suitable solvent.

11. The process of claim 9, wherein the amination process in step (c) comprises the steps of:
(c3) reacting the intermediate of formula III with a haloboron agent and/or a bifluoride agent, and
(c4) reacting with an azide aminating reagent.

12. The process of claim 9, wherein step (c) comprises the steps of:
(c5) reacting the intermediate of formula III with an oxidation agent in a suitable solvent to obtain the intermediate of formula IV

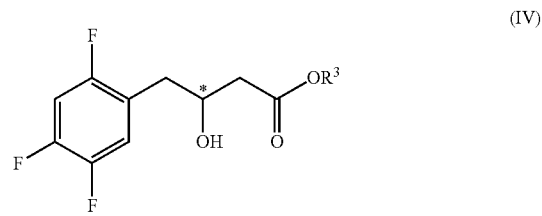

wherein the stereogenic center marked with an * is either in (R)- or (S)-configuration at marked center, or it is in racemic form, and wherein $R^3$ is selected from alkyl residues having from 1 to 6 carbon atoms; and
(c6) reacting the intermediate of formula IV with an aminating agent to obtain an intermediate of formula I.

13. The process of claim 1 comprising the steps of:
(a) providing an intermediate of formula II,

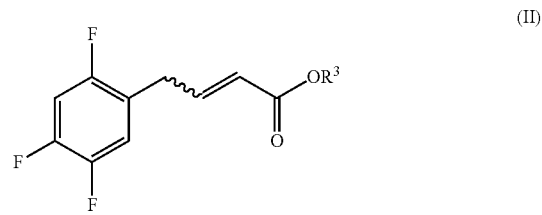

wherein $R^3$ is selected from alkyl residues having from 1 to 6 carbon atoms;
(b) reacting the intermediate of formula II with a borating agent in a suitable solvent to obtain an intermediate of formula III,

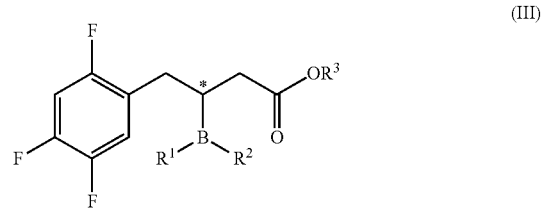

wherein the stereogenic center marked with an * is either in (R)- or (S)-configuration at marked center, or it is in racemic form, and
wherein $R^1$ and $R^2$ are identical or different, and are selected from
(i) alkyl or alkoxy residues, each having from 1 to 12 carbon atoms, wherein each alkyl or alkoxy residue is optionally aryl substituted,
(ii) aryl or aryloxy residues, each having from 6 to 14 carbon atoms, wherein each aryl or aryloxy residue is optionally alkyl substituted;

(iii) halides; and (iv) wherein $R^1$ and $R^2$ optionally form a chiral or nonchiral 5 to 10 membered mono or bicyclic ring, wherein the ring is optionally substituted at least one position with an alkyl residue having from 1 to 12 carbon atoms and/or an aryl residue having from 6 to 14 carbon atoms, and wherein $R^1$ and $R^2$ optionally form an O-benzenedioxy residue;

And $R^3$ is selected from alkyl residues having from 1 to 6 carbon atoms; and (c) converting the intermediate of formula III to the intermediate of formula I, wherein step (c) comprises the steps of:

(c5) reacting the intermediate of formula III with an oxidation agent in a suitable solvent to obtain the intermediate of formula IV,

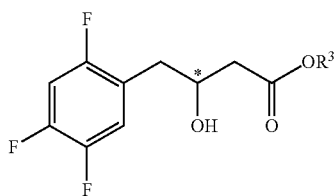

(IV)

wherein the stereogenic center marked with an * is either in (R)- or (S)-configuration at marked center, or it is in racemic form, and wherein $R^3$ is same as above; and (c6') reacting the intermediate of formula IV with an aminating agent, alkyl nitriles, aryl nitriles, each having a formula Xa or Xb, $R^4CN$ (Xa) $R^5CN$ (Xb)

wherein $R^4$ and $R^5$ are alkoxycarbonyl residues optionally chiral, having from 2 to 13 carbon atoms, aryloxycarbonyl residues optionally chiral, having from 7 to 25 carbon atoms to obtain an intermediate of formula I',

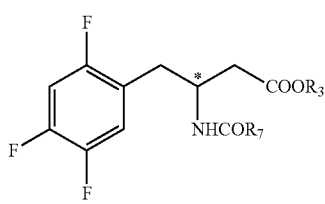

(I')

wherein the stereogenic center marked with an * is either in (R)- or (S)-configuration at marked center, or it is in racemic form and wherein $R^3$ is same as above and $R^7$ is selected from alkyl residues having from 1 to 6 carbon atoms and aryl residues, having from 6 to 24 carbon atoms, optionally substituted, and wherein step (b) and step (c5) occur in one-pot.

14. The process of claim 12, wherein step (c6) is a transition metal catalyzed process using a catalyst comprising a transition metal compound and optionally at least one ligand, wherein the transition metal compound is selected from a gold compound; a rhodium compound; an iron compound; an iridium compound; and a ruthenium compound; or wherein step (c6') is an acid catalyzed process, wherein the acid is selected from Brønsted acids, methanesulfonic acid, chlorsulfonic acid p-toluenesulfonic acid (PTSA), 2,5-dinitrobenzenesulfonic acid (DNBSA), sulfuric acid or dodecylbenzenesulfonic acid (DBSA).

15. An intermediate of formula I', and the isomers, and the isomer mixtures thereof

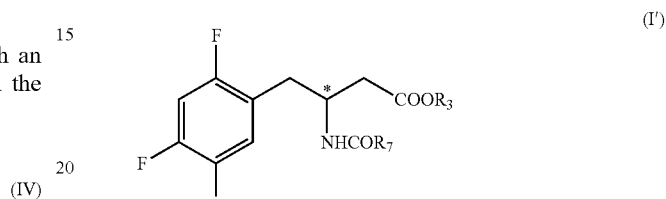

(I')

wherein the stereogenic center marked with an * is either in (R)- or (S)-configuration at marked center, or it is in racemic form and wherein $R^3$ is selected from alkyl residues having from 1 to 6 carbon atoms; and $R^7$ is selected from alkyl residues having from 1 to 6 carbon atoms and aryl residues, having from 6 to 24 carbon atoms optionally substituted with the proviso that $R^3$ or $R^7$ is not a methyl group.

16. An intermediate of formula III, and the isomers, and the isomer mixtures thereof,

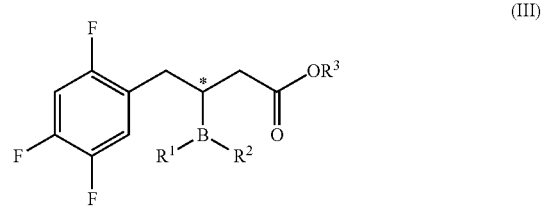

(III)

wherein $R^1$ and $R^2$ are identical or different, and are selected from (i) alkyl or alkoxy residues, each having from 1 to 12 carbon atoms, wherein each alkyl or alkoxy residue is optionally aryl substituted;

(ii) aryl or aryloxy residues, each having from 6 to 14 carbon atoms, wherein each aryl or aryloxy residue is optionally alkyl substituted;

(iii) halides; and (iv) wherein $R^1$ and $R^2$ optionally form a chiral or nonchiral 5 to 10 membered mono or bicyclic ring, wherein the ring is optionally substituted at least one position with an alkyl residue having from 1 to 12 carbon atoms and/or an aryl residue having from 6 to 14 carbon atoms, and wherein $R^1$ and $R^2$ optionally from a O-benzenedioxy residue;

and wherein $R^3$ is selected from alkyl residues having from 1 to 6 carbon atoms.

17. The intermediate of claim 16, having the formula

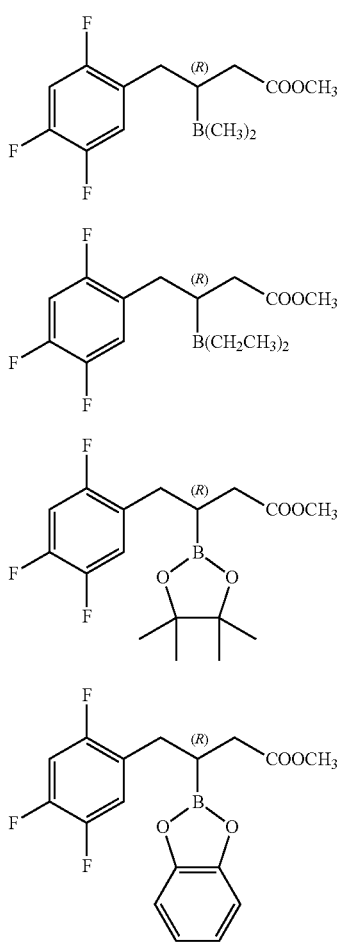

wherein the stereogenic center marked with an * is either in (R)- or (S)-configuration at marked center, or it is in racemic form.

18. A process for the preparation of an intermediate of formula II

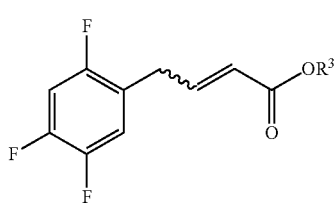

wherein $R^3$ is selected from alkyl residues having from 1 to 6 carbon atoms;

the process comprises the steps of:

(a) providing an intermediate of formula V

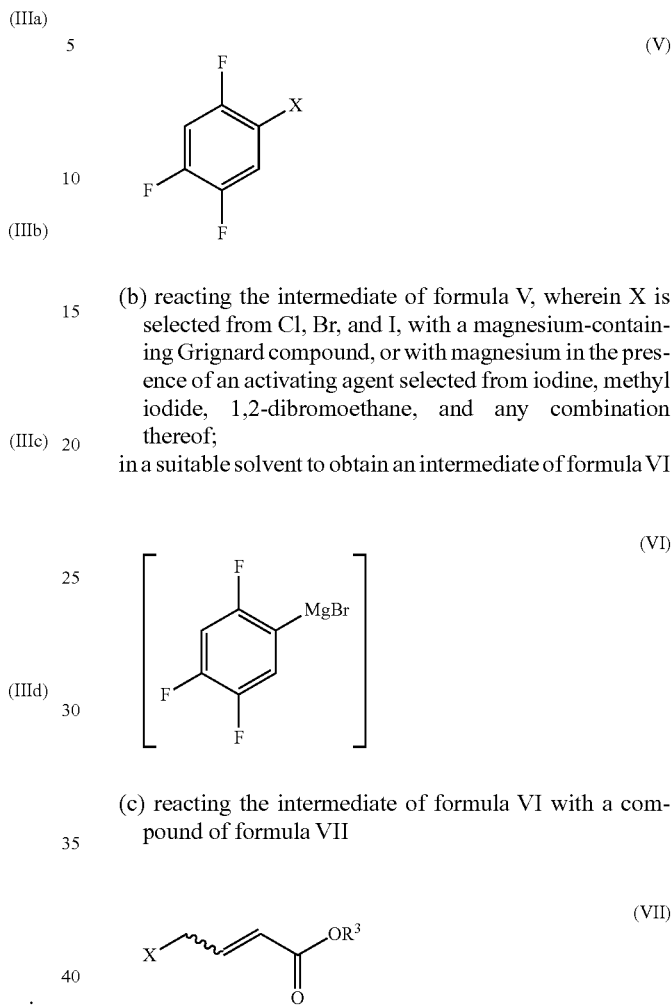

(b) reacting the intermediate of formula V, wherein X is selected from Cl, Br, and I, with a magnesium-containing Grignard compound, or with magnesium in the presence of an activating agent selected from iodine, methyl iodide, 1,2-dibromoethane, and any combination thereof;

in a suitable solvent to obtain an intermediate of formula VI (c) reacting the intermediate of formula VI with a compound of formula VII wherein X is selected from Cl, Br, and I,
wherein $R^3$ is same as above;
in a metal catalyzed cross-coupling process in a suitable solvent to obtain the intermediate of formula II.

19. The process of claim 18, wherein in step (b) the Grignard compound has the formula $R^6MgX$, wherein X is selected from Cl, Br or I, and
wherein $R^6$ is an alkyl residue having from 1 to 6 carbon atoms.

20. The process of claim 18, wherein in step (c) the metal catalyzed cross-coupling process is carried out using a catalyst comprising a metal compound, wherein the metal compound is selected from a cobalt(II) compound, a cobalt(III) compound, an iron(III) compound, iron(II) compound and a manganese(II) compound.

* * * * *